(12) United States Patent
Christianson et al.

(10) Patent No.: US 11,273,033 B2
(45) Date of Patent: *Mar. 15, 2022

(54) SIDE-DELIVERED TRANSCATHETER HEART VALVE REPLACEMENT

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US)

(73) Assignee: VDyne, Inc., Maple Grove, MN (US)

( * ) Notice: Subject to any disclaimer, the term of this patent is extended or adjusted under 35 U.S.C. 154(b) by 452 days.

This patent is subject to a terminal disclaimer.

(21) Appl. No.: 16/443,862

(22) Filed: Jun. 17, 2019

(65) Prior Publication Data

US 2021/0000592 A1 Jan. 7, 2021

Related U.S. Application Data

(63) Continuation of application No. 16/155,890, filed on Oct. 10, 2018, now Pat. No. 10,321,995.

(Continued)

(51) Int. Cl.
*A61F 2/24* (2006.01)
*A61F 2/95* (2013.01)

(52) U.S. Cl.
CPC .......... *A61F 2/2427* (2013.01); *A61F 2/2409* (2013.01); *A61F 2/2412* (2013.01);
(Continued)

(58) Field of Classification Search
CPC .... A61F 2/2427; A61F 2/2409; A61F 2/2412; A61F 2/2418; A61F 2/2433;
(Continued)

(56) References Cited

U.S. PATENT DOCUMENTS

| 3,744,060 A | 7/1973 | Bellhouse et al. |
| 4,079,468 A | 3/1978 | Liotta et al. |

(Continued)

FOREIGN PATENT DOCUMENTS

| AU | 2006203686 B2 | 11/2008 |
| AU | 2009219415 A1 | 9/2009 |

(Continued)

OTHER PUBLICATIONS

International Search Report and Written Opinion for International Application No. PCT/US2019/028822, dated Oct. 24, 2019, 14 pages.

(Continued)

*Primary Examiner* — Katherine M Rodjom

(57) ABSTRACT

The invention relates to a transcatheter heart valve replacement (A61F2/2412), and in particular a side delivered transcatheter prosthetic valve having a tubular frame with a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, and wherein the valve has a height of about 5-60 mm and a diameter of about 25-80 mm.

30 Claims, 29 Drawing Sheets

Related U.S. Application Data

(60) Provisional application No. 62/766,611, filed on Sep. 20, 2018.

(52) U.S. Cl.
CPC .......... *A61F 2/2418* (2013.01); *A61F 2/2433* (2013.01); *A61F 2/95* (2013.01); *A61F 2210/0014* (2013.01); *A61F 2220/0008* (2013.01); *A61F 2220/0016* (2013.01); *A61F 2220/0075* (2013.01); *A61F 2230/001* (2013.01); *A61F 2230/0006* (2013.01); *A61F 2230/0069* (2013.01); *A61F 2250/0039* (2013.01)

(58) Field of Classification Search
CPC .. A61F 2/2436; A61F 2/95; A61F 2220/0016; A61F 2230/001; A61F 2230/0069
See application file for complete search history.

(56) References Cited

U.S. PATENT DOCUMENTS

| | | | |
|---|---|---|---|
| 5,397,351 | A | 3/1995 | Pavcnik |
| 5,509,428 | A | 4/1996 | Dunlop |
| 5,554,185 | A | 9/1996 | Block et al. |
| 6,006,134 | A | 12/1999 | Hill et al. |
| 6,197,013 | B1 | 3/2001 | Reed |
| 6,290,719 | B1 | 9/2001 | Garberoglio |
| 6,449,507 | B1 | 9/2002 | Hill et al. |
| 6,458,153 | B1 | 10/2002 | Bailey et al. |
| 6,532,388 | B1 | 3/2003 | Hill et al. |
| 6,582,467 | B1 | 6/2003 | Teitelbaum |
| 6,628,987 | B1 | 9/2003 | Hill et al. |
| 6,669,724 | B2 | 12/2003 | Park et al. |
| 6,718,208 | B2 | 4/2004 | Hill et al. |
| 6,769,434 | B2 | 8/2004 | Liddicoat et al. |
| 6,890,330 | B2 | 5/2005 | Streeter et al. |
| 6,896,690 | B1 | 5/2005 | Lambrecht et al. |
| 6,904,318 | B2 | 6/2005 | Hill et al. |
| 6,929,653 | B2 | 8/2005 | Streeter |
| 7,074,189 | B1 | 7/2006 | Montegrande |
| 7,125,418 | B2 | 10/2006 | Duran |
| 7,175,660 | B2 | 2/2007 | Cartledge et al. |
| 7,201,761 | B2 | 4/2007 | Woolfson et al. |
| 7,225,019 | B2 | 5/2007 | Jahns et al. |
| 7,269,457 | B2 | 9/2007 | Shafer et al. |
| 7,331,991 | B2 | 2/2008 | Kheradvar |
| 7,361,189 | B2 | 4/2008 | Case et al. |
| 7,374,571 | B2 | 5/2008 | Pease |
| 7,442,204 | B2 | 10/2008 | Schwammenthal et al. |
| 7,449,027 | B2 | 11/2008 | Hunt |
| 7,621,948 | B2 | 11/2009 | Herrmann et al. |
| 7,648,527 | B2 | 1/2010 | Agnew |
| 7,717,952 | B2 | 5/2010 | Case |
| 7,749,245 | B2 | 7/2010 | Cohn et al. |
| 7,753,949 | B2 | 7/2010 | Lamphere |
| 7,811,316 | B2 | 10/2010 | Kalmann et al. |
| 7,828,840 | B2 | 11/2010 | Biggs |
| 7,846,199 | B2 | 12/2010 | Paul |
| 8,303,648 | B2 | 11/2012 | Grewe |
| 8,366,768 | B2 | 2/2013 | Zhang |
| 8,491,650 | B2 | 7/2013 | Wiemeyer |
| 8,568,474 | B2 | 10/2013 | Yeung |
| 8,628,571 | B1 | 1/2014 | Hacohen et al. |
| 8,641,752 | B1 | 2/2014 | Holm |
| 8,696,743 | B2 | 4/2014 | Holecek |
| 8,728,153 | B2 | 5/2014 | Bishop |
| 8,758,395 | B2 | 6/2014 | Kleshinski |
| 8,846,390 | B2 | 9/2014 | Dove |
| 8,876,892 | B2 | 11/2014 | Tran |
| 8,900,295 | B2 | 12/2014 | Migliazza et al. |
| 8,915,958 | B2 | 12/2014 | Braido |
| 8,926,690 | B2 | 1/2015 | Kovalsky |
| 8,926,692 | B2 | 1/2015 | Dwork |
| 8,926,694 | B2 | 1/2015 | Costello |
| 8,940,044 | B2 | 1/2015 | Hammer |
| 8,956,404 | B2 | 2/2015 | Börtlein |
| 8,986,370 | B2 | 3/2015 | Annest et al. |
| 9,011,524 | B2 | 4/2015 | Eberhardt |
| 9,017,399 | B2 | 4/2015 | Gross |
| 9,050,188 | B2 | 4/2015 | Schweich |
| 9,072,604 | B1 | 7/2015 | Melnick |
| 9,119,714 | B2 | 9/2015 | Shandas |
| 9,216,076 | B2 | 12/2015 | Mitra |
| 9,232,995 | B2 | 1/2016 | Kovalsky et al. |
| 9,241,792 | B2 | 1/2016 | Benichou |
| 9,248,016 | B2 | 2/2016 | Oba |
| 9,259,215 | B2 | 2/2016 | Chou |
| 9,277,990 | B2 | 3/2016 | Klima |
| 9,289,282 | B2 | 3/2016 | Olson |
| 9,289,296 | B2 | 3/2016 | Braido |
| 9,295,547 | B2 | 3/2016 | Costello |
| 9,301,839 | B2 | 4/2016 | Stante |
| 9,308,086 | B2 | 4/2016 | Ho |
| 9,456,899 | B2 | 4/2016 | Yeung |
| 9,339,367 | B2 | 5/2016 | Carpenter |
| 9,370,418 | B2 | 6/2016 | Pintor |
| 9,381,083 | B2 | 7/2016 | Costello |
| 9,387,075 | B2 | 7/2016 | Börtlein |
| 9,393,111 | B2 | 7/2016 | Ma |
| 9,414,915 | B2 | 8/2016 | Lombardi et al. |
| 9,433,500 | B2 | 9/2016 | Chau |
| 9,440,054 | B2 | 9/2016 | Bishop |
| 9,468,525 | B2 | 10/2016 | Kovalsky et al. |
| 9,474,604 | B2 | 10/2016 | Centola |
| 9,486,306 | B2 | 11/2016 | Tegels |
| 9,510,941 | B2 | 12/2016 | Bishop |
| 9,554,902 | B2 | 1/2017 | Braido |
| 9,579,196 | B2 | 2/2017 | Morriss |
| 9,579,200 | B2 | 2/2017 | Lederman |
| 9,610,159 | B2 | 4/2017 | Christianson |
| 9,615,925 | B2 | 4/2017 | Subramanian |
| 9,629,719 | B2 | 4/2017 | Rothstein |
| 9,636,222 | B2 | 5/2017 | Oslund |
| 9,649,191 | B2 | 5/2017 | Savage |
| 9,662,202 | B2 | 5/2017 | Quill et al. |
| 9,662,203 | B2 | 5/2017 | Sheehan |
| 9,662,209 | B2 | 5/2017 | Gross |
| 9,675,454 | B2 | 6/2017 | Vidlund |
| 9,675,485 | B2 | 6/2017 | Essinger |
| 9,687,343 | B2 | 6/2017 | Bortlein |
| 9,707,076 | B2 | 7/2017 | Stack |
| 9,713,530 | B2 | 7/2017 | Cabiri |
| 9,750,607 | B2 | 9/2017 | Ganesan |
| 9,763,778 | B2 | 9/2017 | Börtlein |
| 9,763,779 | B2 | 9/2017 | Börtlein |
| 9,788,946 | B2 | 10/2017 | Bobo, Jr. et al. |
| 9,839,511 | B2 | 12/2017 | Ma |
| 9,849,011 | B2 | 12/2017 | Zimmerman |
| 9,855,384 | B2 | 1/2018 | Cohen |
| 9,861,464 | B2 | 1/2018 | Azimpour |
| 9,895,219 | B2 | 2/2018 | Costello et al. |
| 9,901,330 | B2 | 2/2018 | Akpinar |
| 9,918,838 | B2 | 3/2018 | Ring |
| 9,943,409 | B2 | 4/2018 | Kim |
| 9,949,825 | B2 | 4/2018 | Braido |
| 9,968,444 | B2 | 5/2018 | Millwee |
| 9,968,445 | B2 | 5/2018 | Morriss |
| 9,980,815 | B2 | 5/2018 | Nitzan |
| 9,987,121 | B2 | 6/2018 | Blanzy |
| 10,010,411 | B2 | 7/2018 | Peter |
| 10,010,412 | B2 | 7/2018 | Taft |
| 10,022,054 | B2 | 7/2018 | Najafi |
| 10,022,222 | B2 | 7/2018 | Groothuis |
| 10,022,223 | B2 | 7/2018 | Bruchman |
| 10,028,821 | B2 | 7/2018 | Centola |
| 10,028,831 | B2 | 7/2018 | Morin |
| 10,034,667 | B2 | 7/2018 | Morris |
| 10,034,747 | B2 | 7/2018 | Harewood |
| 10,039,638 | B2 | 8/2018 | Bruchman |
| 10,058,315 | B2 | 8/2018 | Rafiee |
| 10,058,411 | B2 | 8/2018 | Fifer |
| 10,058,421 | B2 | 8/2018 | Arai |

(56) References Cited

U.S. PATENT DOCUMENTS

| | | |
|---|---|---|
| 10,058,426 B2 | 8/2018 | Barbarino |
| 10,064,405 B2 | 9/2018 | Dale |
| 10,080,653 B2 | 9/2018 | Conklin |
| 10,085,835 B2 | 10/2018 | Thambar |
| 10,105,224 B2 | 10/2018 | Buchbinder |
| 10,117,741 B2 | 11/2018 | Schweich |
| 10,123,874 B2 | 11/2018 | Khairkhahan |
| 10,130,331 B2 | 11/2018 | Stigall |
| 10,130,467 B2 | 11/2018 | Braido |
| 10,149,685 B2 | 12/2018 | Kizuka |
| 10,154,905 B2 | 12/2018 | Duffy |
| 10,179,043 B2 | 1/2019 | Cohen-Tzemach |
| 10,182,908 B2 | 1/2019 | Tubishevitz |
| 10,182,911 B2 | 1/2019 | Hillukka |
| 10,206,775 B2 | 2/2019 | Kovalsky |
| 10,219,895 B2 | 3/2019 | Wagner |
| 10,219,896 B2 | 3/2019 | Sandstrom |
| 10,220,192 B2 | 3/2019 | Drasier |
| 10,226,178 B2 | 3/2019 | Cohen |
| 10,226,333 B2 | 3/2019 | Cartledge |
| 10,226,335 B2 | 3/2019 | Cartledge et al. |
| 10,245,142 B2 | 4/2019 | Bonhoeffer |
| 10,258,467 B2 | 4/2019 | Hou |
| 10,265,173 B2 | 4/2019 | Griffin |
| 10,321,987 B2 | 6/2019 | Wang |
| 10,321,995 B1 | 6/2019 | Christianson et al. |
| 10,327,895 B2 | 6/2019 | Lozonschi |
| 10,327,899 B2 | 6/2019 | Sandstrom |
| 10,329,066 B2 | 6/2019 | Kruetzfeldt |
| 10,350,047 B2 | 7/2019 | Rajpara |
| 10,357,361 B2 | 7/2019 | Rafi |
| 10,368,989 B2 | 8/2019 | Duffy |
| 10,398,550 B2 | 9/2019 | Chalekian |
| 10,426,611 B2 | 10/2019 | Hariton |
| 10,433,957 B2 | 10/2019 | Khouengboua |
| 10,433,960 B1 | 10/2019 | Sutherland |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund, I et al. |
| 11,173,027 B2 | 11/2021 | Christianson et al. |
| 2003/0040772 A1 | 2/2003 | Hyodoh et al. |
| 2003/0040808 A1 | 2/2003 | Stack et al. |
| 2003/0153901 A1 | 8/2003 | Herweck |
| 2003/0166990 A1 | 9/2003 | Trauthen |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0015167 A1 | 1/2006 | Armstrong |
| 2006/0190075 A1 | 8/2006 | Jordan et al. |
| 2006/0195180 A1 | 8/2006 | Kheradvar |
| 2006/0229708 A1 | 10/2006 | Powell et al. |
| 2006/0241745 A1 | 10/2006 | Solem |
| 2006/0271098 A1 | 11/2006 | Peacock |
| 2006/0276887 A1 | 12/2006 | Brady et al. |
| 2007/0016286 A1 | 1/2007 | Herrmann et al. |
| 2007/0027535 A1 | 2/2007 | Purdy |
| 2007/0032850 A1 | 2/2007 | Ruiz |
| 2007/0038295 A1 | 2/2007 | Case |
| 2007/0100427 A1 | 5/2007 | Perouse |
| 2007/0162102 A1 | 7/2007 | Ryan |
| 2007/0208417 A1 | 9/2007 | Agnew |
| 2007/0213805 A1 | 9/2007 | Schaeffer |
| 2007/0233176 A1 | 10/2007 | Gilsen |
| 2007/0233228 A1 | 10/2007 | Eberhardt |
| 2007/0239271 A1 | 10/2007 | Nguyen |
| 2007/0288087 A1 | 12/2007 | Fearnot |
| 2008/0004686 A1 | 1/2008 | Hunt |
| 2008/0020013 A1 | 1/2008 | Reyes |
| 2008/0065204 A1 | 3/2008 | Macoviak et al. |
| 2008/0071287 A1 | 3/2008 | Goto |
| 2008/0132999 A1 | 6/2008 | Mericle |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul |
| 2008/0200980 A1 | 8/2008 | Robin et al. |
| 2008/0208332 A1 | 8/2008 | Lamphere |
| 2008/0221672 A1 | 9/2008 | Lamphere et al. |
| 2008/0262592 A1 | 10/2008 | Jordan et al. |
| 2008/0262609 A1 | 10/2008 | Gross |
| 2008/0275550 A1 | 11/2008 | Kheradvar |
| 2009/0005863 A1 | 1/2009 | Goetz et al. |
| 2009/0054976 A1 | 2/2009 | Tuval et al. |
| 2009/0094189 A1 | 4/2009 | Macauley |
| 2009/0192586 A1 | 7/2009 | Tabor |
| 2009/0254174 A1 | 10/2009 | Case |
| 2009/0264991 A1 | 10/2009 | Paul |
| 2009/0287290 A1 | 11/2009 | Macaulay |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen |
| 2010/0161043 A1 | 6/2010 | Maisano |
| 2010/0168844 A1 | 7/2010 | Toomes |
| 2010/0174363 A1 | 7/2010 | Castro |
| 2010/0179583 A1 | 7/2010 | Carpenter |
| 2010/0179584 A1 | 7/2010 | Carpenter |
| 2010/0179647 A1 | 7/2010 | Carpenter |
| 2010/0280591 A1 | 11/2010 | Shin et al. |
| 2010/0298929 A1 | 11/2010 | Thornton et al. |
| 2010/0305685 A1 | 12/2010 | Millwee |
| 2011/0004237 A1 | 1/2011 | Schneider et al. |
| 2011/0029071 A1 | 2/2011 | Zlotnick |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung |
| 2011/0125145 A1 | 5/2011 | Mody |
| 2011/0137397 A1 | 6/2011 | Chau et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson |
| 2012/0022639 A1 | 1/2012 | Hacohen et al. |
| 2012/0022640 A1 | 1/2012 | Gross |
| 2012/0022644 A1 | 1/2012 | Reich |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima |
| 2012/0137521 A1 | 6/2012 | Millwee |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid |
| 2012/0232574 A1 | 9/2012 | Kim |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0055941 A1 | 3/2013 | Holecek |

(56) References Cited

U.S. PATENT DOCUMENTS

| | | |
|---|---|---|
| 2013/0131714 A1 | 5/2013 | Wang |
| 2013/0131792 A1 | 5/2013 | Miller |
| 2013/0166017 A1 | 6/2013 | Cartledge et al. |
| 2013/0184742 A1 | 7/2013 | Ganesan |
| 2013/0190857 A1 | 7/2013 | Mitra |
| 2013/0190861 A1 | 7/2013 | Chau et al. |
| 2013/0197621 A1 | 8/2013 | Ryan |
| 2013/0226289 A1 | 8/2013 | Shaolian |
| 2013/0238010 A1 | 9/2013 | Johnson |
| 2013/0238089 A1* | 9/2013 | Lichtenstein ......... A61F 2/2412 623/2.11 |
| 2013/0253570 A1 | 9/2013 | Bates |
| 2013/0274618 A1 | 10/2013 | Hou |
| 2013/0274855 A1 | 10/2013 | Stante |
| 2013/0282110 A1 | 10/2013 | Schweich |
| 2013/0297010 A1 | 11/2013 | Bishop |
| 2013/0304197 A1 | 11/2013 | Buchbinder et al. |
| 2013/0304200 A1 | 11/2013 | McLean et al. |
| 2013/0331929 A1 | 12/2013 | Mitra |
| 2013/0338764 A1 | 12/2013 | Thornton et al. |
| 2014/0000112 A1 | 1/2014 | Braido |
| 2014/0005540 A1 | 1/2014 | Merhi |
| 2014/0005768 A1 | 1/2014 | Thomas |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0039511 A1 | 2/2014 | Morris |
| 2014/0039611 A1 | 2/2014 | Lane et al. |
| 2014/0052237 A1 | 2/2014 | Lane et al. |
| 2014/0081383 A1 | 3/2014 | Eberhardt |
| 2014/0088680 A1 | 3/2014 | Costello |
| 2014/0107758 A1 | 4/2014 | Glazier |
| 2014/0110279 A1 | 4/2014 | Kruetzfeldt |
| 2014/0114403 A1 | 4/2014 | Dale |
| 2014/0121763 A1 | 5/2014 | Duffy et al. |
| 2014/0135895 A1 | 5/2014 | Andress |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett |
| 2014/0194704 A1 | 7/2014 | Millett |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund |
| 2014/0222136 A1 | 8/2014 | Geist et al. |
| 2014/0222137 A1 | 8/2014 | Miller |
| 2014/0222142 A1* | 8/2014 | Kovalsky ............... A61F 2/2436 623/2.17 |
| 2014/0249566 A1 | 9/2014 | Quinn |
| 2014/0257466 A1 | 9/2014 | Board et al. |
| 2014/0257467 A1 | 9/2014 | Lane et al. |
| 2014/0276616 A1 | 9/2014 | Smith |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels |
| 2014/0303718 A1 | 10/2014 | Tegels |
| 2014/0303724 A1 | 10/2014 | Bluestein |
| 2014/0309732 A1 | 10/2014 | Solem |
| 2014/0324161 A1 | 10/2014 | Tegels |
| 2014/0350662 A1 | 11/2014 | Vaturi |
| 2014/0358224 A1 | 12/2014 | Tegels et al. |
| 2014/0371789 A1 | 12/2014 | Harton |
| 2014/0379076 A1 | 12/2014 | Vidlund et al. |
| 2015/0005808 A1 | 1/2015 | Chouinard |
| 2015/0005874 A1 | 1/2015 | Vidlund |
| 2015/0039081 A1* | 2/2015 | Costello ............... A61F 2/2436 623/2.11 |
| 2015/0045880 A1 | 2/2015 | Hacohen |
| 2015/0051687 A1 | 2/2015 | Dickerhoff |
| 2015/0094802 A1 | 4/2015 | Buchbinder |
| 2015/0112188 A1 | 4/2015 | Stigall |
| 2015/0119982 A1 | 4/2015 | Quill |
| 2015/0127093 A1 | 5/2015 | Hosmer |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau |
| 2015/0216661 A1 | 8/2015 | Hacohen |
| 2015/0230919 A1 | 8/2015 | Chau |
| 2015/0245934 A1 | 9/2015 | Lombardi |
| 2015/0257878 A1 | 9/2015 | Lane et al. |
| 2015/0257880 A1 | 9/2015 | Börtlein |
| 2015/0257882 A1 | 9/2015 | Börtlein |
| 2015/0265400 A1 | 9/2015 | Eidenschink et al. |
| 2015/0272731 A1 | 10/2015 | Racchini |
| 2015/0282922 A1 | 10/2015 | Hingston et al. |
| 2015/0282931 A1 | 10/2015 | Brunnett et al. |
| 2015/0289971 A1 | 10/2015 | Costello |
| 2015/0289975 A1 | 10/2015 | Costello |
| 2015/0297241 A1 | 10/2015 | Yodfat |
| 2015/0305867 A1 | 10/2015 | Liu |
| 2015/0313701 A1 | 11/2015 | Krahbichler |
| 2015/0335424 A1 | 11/2015 | McLean et al. |
| 2015/0342717 A1 | 12/2015 | O'Donnell |
| 2015/0351904 A1 | 12/2015 | Cooper |
| 2015/0351906 A1 | 12/2015 | Hammer et al. |
| 2015/0351910 A1 | 12/2015 | Gilmore et al. |
| 2015/0359629 A1 | 12/2015 | Ganesan |
| 2016/0008130 A1 | 1/2016 | Hasin |
| 2016/0008131 A1 | 1/2016 | Christianson et al. |
| 2016/0022417 A1 | 1/2016 | Karapetian |
| 2016/0030165 A1 | 2/2016 | Mitra |
| 2016/0030167 A1 | 2/2016 | Delaloye |
| 2016/0038280 A1 | 2/2016 | Morriss et al. |
| 2016/0038283 A1 | 2/2016 | Divekar |
| 2016/0045165 A1 | 2/2016 | Braido |
| 2016/0045306 A1 | 2/2016 | Agrawal |
| 2016/0045309 A1 | 2/2016 | Valdez |
| 2016/0067031 A1 | 3/2016 | Kassab |
| 2016/0081799 A1 | 3/2016 | Leo |
| 2016/0095703 A1 | 4/2016 | Thomas |
| 2016/0095704 A1 | 4/2016 | Whitman |
| 2016/0113764 A1 | 4/2016 | Sheahan |
| 2016/0113766 A1 | 4/2016 | Ganesan |
| 2016/0113768 A1 | 4/2016 | Ganesan |
| 2016/0143721 A1 | 5/2016 | Rosenbluth |
| 2016/0143730 A1 | 5/2016 | Kheradvar |
| 2016/0143735 A1 | 5/2016 | Subramanian |
| 2016/0143739 A1 | 5/2016 | Horgan |
| 2016/0158004 A1 | 6/2016 | Kumar |
| 2016/0158007 A1 | 6/2016 | Centola |
| 2016/0158008 A1 | 6/2016 | Miller |
| 2016/0166382 A1 | 6/2016 | Nguyen |
| 2016/0184488 A1 | 6/2016 | Toyoda |
| 2016/0194425 A1 | 7/2016 | Mitra |
| 2016/0213470 A1 | 7/2016 | Ahlberg |
| 2016/0213473 A1 | 7/2016 | Hacohen et al. |
| 2016/0220367 A1 | 8/2016 | Barrett |
| 2016/0220372 A1 | 8/2016 | Medema |
| 2016/0220734 A1 | 8/2016 | Dyamenahalli |
| 2016/0228250 A1 | 8/2016 | Casley |
| 2016/0235530 A1 | 8/2016 | Thomas |
| 2016/0256269 A1 | 9/2016 | Cahalane |
| 2016/0256270 A1 | 9/2016 | Folan |
| 2016/0270911 A1 | 9/2016 | Ganesan |
| 2016/0303804 A1 | 10/2016 | Grbic |
| 2016/0310274 A1 | 10/2016 | Gross |
| 2016/0317301 A1 | 11/2016 | Quadri |
| 2016/0324633 A1 | 11/2016 | Gross et al. |
| 2016/0324639 A1 | 11/2016 | Nguyen |
| 2016/0331534 A1 | 11/2016 | Buchbinder |
| 2016/0354201 A1 | 12/2016 | Keogh |
| 2016/0361169 A1 | 12/2016 | Gross |
| 2016/0361184 A1 | 12/2016 | Tabor |
| 2016/0367360 A1 | 12/2016 | Cartledge et al. |
| 2016/0367364 A1 | 12/2016 | Torrianni |
| 2017/0000603 A1 | 1/2017 | Conklin |

(56) References Cited

U.S. PATENT DOCUMENTS

| | | |
|---|---|---|
| 2017/0000604 A1 | 1/2017 | Conklin |
| 2017/0020670 A1 | 1/2017 | Murray et al. |
| 2017/0035562 A1 | 2/2017 | Quadri |
| 2017/0035568 A1 | 2/2017 | Lombardi et al. |
| 2017/0056166 A1 | 3/2017 | Ratz et al. |
| 2017/0056171 A1 | 3/2017 | Cooper |
| 2017/0071733 A1 | 3/2017 | Ghione et al. |
| 2017/0071736 A1 | 3/2017 | Zhu |
| 2017/0076014 A1 | 3/2017 | Bressloff |
| 2017/0079786 A1 | 3/2017 | Li |
| 2017/0079795 A1 | 3/2017 | Morrissey |
| 2017/0100246 A1 | 4/2017 | Rust |
| 2017/0112620 A1 | 4/2017 | Curley |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich |
| 2017/0196690 A1 | 7/2017 | Racchini |
| 2017/0209266 A1 | 7/2017 | Lane |
| 2017/0209268 A1 | 7/2017 | Cunningham et al. |
| 2017/0216026 A1 | 8/2017 | Quill et al. |
| 2017/0216030 A1 | 8/2017 | Joensson |
| 2017/0224480 A1 | 8/2017 | Garde |
| 2017/0224486 A1 | 8/2017 | Delaloye |
| 2017/0231755 A1 | 8/2017 | Gloss |
| 2017/0231760 A1 | 8/2017 | Lane |
| 2017/0239047 A1 | 8/2017 | Quill |
| 2017/0245993 A1 | 8/2017 | Gross et al. |
| 2017/0245994 A1 | 8/2017 | Khairkhahan |
| 2017/0252163 A1 | 9/2017 | Kheradvar |
| 2017/0258584 A1 | 9/2017 | Chang |
| 2017/0258585 A1 | 9/2017 | Marquez |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross |
| 2017/0325948 A1 | 11/2017 | Wallace et al. |
| 2017/0325976 A1 | 11/2017 | Nguyen |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane |
| 2017/0360557 A1 | 12/2017 | Kheradvar et al. |
| 2017/0360558 A1 | 12/2017 | Ma |
| 2017/0360561 A1 | 12/2017 | Bell |
| 2018/0014932 A1 | 1/2018 | Hammer et al. |
| 2018/0021130 A1 | 1/2018 | Danino |
| 2018/0035971 A1 | 2/2018 | Brenner |
| 2018/0042549 A1 | 2/2018 | Ho |
| 2018/0042723 A1 | 2/2018 | Yellin |
| 2018/0043133 A1 | 2/2018 | Wong |
| 2018/0049875 A1 | 2/2018 | Iflah |
| 2018/0049876 A1 | 2/2018 | Miraki |
| 2018/0055628 A1 | 3/2018 | Patel |
| 2018/0055633 A1 | 3/2018 | Costello |
| 2018/0056045 A1 | 3/2018 | Donoghue |
| 2018/0056046 A1 | 3/2018 | Kiersey |
| 2018/0071088 A1 | 3/2018 | Badhwar |
| 2018/0078367 A1 | 3/2018 | Saar |
| 2018/0078368 A1 | 3/2018 | Vidlund |
| 2018/0078370 A1 | 3/2018 | Kovalsky |
| 2018/0085219 A1 | 3/2018 | Krivoruchko |
| 2018/0098837 A1 | 4/2018 | Shahriari |
| 2018/0099124 A1 | 4/2018 | McLoughlin |
| 2018/0116793 A1 | 5/2018 | Salahieh et al. |
| 2018/0116843 A1 | 5/2018 | Schreck |
| 2018/0125642 A1 | 5/2018 | White |
| 2018/0125654 A1 | 5/2018 | Duffy |
| 2018/0126127 A1 | 5/2018 | Devereux |
| 2018/0133000 A1 | 5/2018 | Scheinblum |
| 2018/0133006 A1 | 5/2018 | Jones |
| 2018/0133011 A1 | 5/2018 | Perouse |
| 2018/0140417 A1 | 5/2018 | Sciscio |
| 2018/0147041 A1 | 5/2018 | Chouinard |
| 2018/0147055 A1 | 5/2018 | Vidlund et al. |
| 2018/0153689 A1 | 6/2018 | Maimon et al. |
| 2018/0161158 A1 | 6/2018 | Kovalsky |
| 2018/0161161 A1 | 6/2018 | Yellin |
| 2018/0168793 A1 | 6/2018 | Lees |
| 2018/0177580 A9 | 6/2018 | Shemesh |
| 2018/0177594 A1 | 6/2018 | Patel |
| 2018/0185153 A1 | 7/2018 | Bishop |
| 2018/0193138 A1 | 7/2018 | Vidlund |
| 2018/0200049 A1* | 7/2018 | Chambers .............. A61F 2/2436 |
| 2018/0206983 A1 | 7/2018 | Noe et al. |
| 2018/0214141 A1 | 8/2018 | Mendez |
| 2018/0221016 A1 | 8/2018 | Conklin |
| 2018/0243071 A1 | 8/2018 | Eigler |
| 2018/0243532 A1 | 8/2018 | Willard |
| 2018/0256322 A1 | 9/2018 | Zhang |
| 2018/0256327 A1 | 9/2018 | Perszyk |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung |
| 2018/0289485 A1 | 10/2018 | Rajagopal |
| 2018/0296325 A1 | 10/2018 | McLean |
| 2018/0296335 A1 | 10/2018 | Miyashiro |
| 2018/0296337 A1 | 10/2018 | Duhay |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler |
| 2018/0318073 A1 | 11/2018 | Tseng |
| 2018/0318078 A1 | 11/2018 | Willard |
| 2018/0325665 A1 | 11/2018 | Gurovich |
| 2018/0325671 A1 | 11/2018 | Abunassar |
| 2018/0338832 A1 | 11/2018 | Ganesan |
| 2018/0344456 A1 | 12/2018 | Barash et al. |
| 2018/0353293 A1 | 12/2018 | Colavito |
| 2018/0353295 A1 | 12/2018 | Cooper |
| 2018/0360439 A1 | 12/2018 | Niland |
| 2018/0360599 A1 | 12/2018 | Drasler |
| 2019/0000619 A1 | 1/2019 | Quijano et al. |
| 2019/0008640 A1 | 1/2019 | Cooper |
| 2019/0015188 A1 | 1/2019 | Eigler |
| 2019/0021834 A1 | 1/2019 | Nir |
| 2019/0029819 A1 | 1/2019 | Huber |
| 2019/0029823 A1 | 1/2019 | Nguyen |
| 2019/0038404 A1 | 2/2019 | Iamberger |
| 2019/0038405 A1 | 2/2019 | Iamberger |
| 2019/0053894 A1 | 2/2019 | Levi |
| 2019/0053895 A1 | 2/2019 | Levi |
| 2019/0053897 A1 | 2/2019 | Levi |
| 2019/0053898 A1 | 2/2019 | Maimon |
| 2019/0053899 A1 | 2/2019 | Levi |
| 2019/0060051 A1 | 2/2019 | Scheeff |
| 2019/0060057 A1 | 2/2019 | Cohen et al. |
| 2019/0060059 A1 | 2/2019 | Delgado |
| 2019/0060069 A1 | 2/2019 | Maimon |
| 2019/0060071 A1 | 2/2019 | Lane |
| 2019/0069995 A1 | 3/2019 | Levi et al. |
| 2019/0070003 A1 | 3/2019 | Siegel |
| 2019/0076233 A1 | 3/2019 | Fish |
| 2019/0076249 A1 | 3/2019 | Khairkhahan |
| 2019/0083085 A1 | 3/2019 | Gilmore |
| 2019/0091005 A1 | 3/2019 | Fifer |
| 2019/0091015 A1 | 3/2019 | Dienno |
| 2019/0091018 A1 | 3/2019 | Hariton |
| 2019/0091022 A1 | 3/2019 | Yellin |
| 2019/0099265 A1 | 4/2019 | Braido |
| 2019/0099270 A1 | 4/2019 | Morrissey |
| 2019/0105153 A1 | 4/2019 | Barash |
| 2019/0117223 A1 | 4/2019 | Abunassar |
| 2019/0117387 A1 | 4/2019 | Li |
| 2019/0117391 A1 | 4/2019 | Humair |

(56) References Cited

U.S. PATENT DOCUMENTS

| | | |
|---|---|---|
| 2019/0117400 A1 | 4/2019 | Medema |
| 2019/0117401 A1 | 4/2019 | Cortez |
| 2019/0125287 A1 | 5/2019 | Itou |
| 2019/0125536 A1 | 5/2019 | Prabhu |
| 2019/0133528 A1 | 5/2019 | Kassab |
| 2019/0133756 A1 | 5/2019 | Zhang |
| 2019/0133757 A1 | 5/2019 | Zhang |
| 2019/0133765 A1 | 5/2019 | Yellin |
| 2019/0142566 A1 | 5/2019 | Lansky |
| 2019/0142582 A1 | 5/2019 | Drasler |
| 2019/0150867 A1 | 5/2019 | Itou |
| 2019/0151509 A1 | 5/2019 | Kheradvar |
| 2019/0167423 A1 | 6/2019 | Hariton |
| 2019/0167429 A1 | 6/2019 | Stearns |
| 2019/0175338 A1 | 6/2019 | White |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp |
| 2019/0192287 A1 | 6/2019 | Sandstrom |
| 2019/0192296 A1 | 6/2019 | Schwartz |
| 2019/0209317 A1 | 7/2019 | Zhang |
| 2019/0209320 A1 | 7/2019 | Drasler |
| 2019/0231523 A1 | 8/2019 | Lombardi |
| 2019/0240020 A1 | 8/2019 | Rafiee |
| 2019/0240022 A1 | 8/2019 | Rafiee |
| 2019/0247050 A1 | 8/2019 | Goldsmith |
| 2019/0254815 A1 | 8/2019 | Bruchman |
| 2019/0254816 A1 | 8/2019 | Anderson |
| 2019/0262118 A1 | 8/2019 | Eigler |
| 2019/0262129 A1 | 8/2019 | Cooper |
| 2019/0269413 A1 | 9/2019 | Yodfat |
| 2019/0269504 A1 | 9/2019 | Wang |
| 2019/0269839 A1 | 9/2019 | Wilson |
| 2019/0282360 A1 | 9/2019 | Colavito |
| 2019/0290426 A1 | 9/2019 | Maimon |
| 2019/0290427 A1 | 9/2019 | Mantanus |
| 2019/0307563 A1 | 10/2019 | Sandstrom |
| 2019/0307589 A1 | 10/2019 | Goldberg |
| 2019/0365538 A1 | 12/2019 | Chambers et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund, I et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |

FOREIGN PATENT DOCUMENTS

| | | |
|---|---|---|
| AU | 201123 8752 A1 | 10/2012 |
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2016228261 A1 | 4/2017 |
| AU | 2017210659 A1 | 8/2017 |
| AU | 20143 60294 B2 | 10/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI09093 79 B1 | 9/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 2753853 A1 | 9/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |

(56) References Cited

FOREIGN PATENT DOCUMENTS

| | | | |
|---|---|---|---|
| CN | 10606143 7 | A | 10/2016 |
| CN | 106061437 | A | 10/2016 |
| CN | 106073 946 | A | 11/2016 |
| CN | 106068109 | A | 11/2016 |
| CN | 106073946 | A | 11/2016 |
| CN | 106255475 | A | 12/2016 |
| CN | 103917194 | B | 2/2017 |
| CN | 106456324 | A | 2/2017 |
| CN | 106456325 | A | 2/2017 |
| CN | 105073068 | B | 3/2017 |
| CN | 106470641 | A | 3/2017 |
| CN | 105451684 | B | 4/2017 |
| CN | 106573129 | A | 4/2017 |
| CN | 103945792 | B | 5/2017 |
| CN | 106659394 | A | 5/2017 |
| CN | 106716098 | A | 5/2017 |
| CN | 106794063 | A | 5/2017 |
| CN | 10689003 5 | A | 6/2017 |
| CN | 106890035 | A | 6/2017 |
| CN | 106943207 | A | 7/2017 |
| CN | 106999054 | A | 8/2017 |
| CN | 106999281 | A | 8/2017 |
| CN | 106999281 | A | 8/2017 |
| CN | 104114127 | B | 9/2017 |
| CN | 107115161 | A | 9/2017 |
| CN | 1072603 66 | A | 10/2017 |
| CN | 107249482 | A | 10/2017 |
| CN | 107260366 | A | 10/2017 |
| CN | 104918582 | B | 11/2017 |
| CN | 107374783 | A | 11/2017 |
| CN | 1074273 64 | A | 12/2017 |
| CN | 107427364 | A | 12/2017 |
| CN | 106255476 | B | 1/2018 |
| CN | 107530157 | A | 1/2018 |
| CN | 107530167 | A | 1/2018 |
| CN | 107530177 | A | 1/2018 |
| CN | 107613908 | A | 1/2018 |
| CN | 104869948 | B | 2/2018 |
| CN | 107714240 | A | 2/2018 |
| CN | 107920897 | A | 4/2018 |
| CN | 104853696 | B | 6/2018 |
| CN | 108135696 | A | 6/2018 |
| CN | 108430392 | A | 8/2018 |
| CN | 108472142 | A | 8/2018 |
| CN | 106726007 | B | 11/2018 |
| CN | 109124829 | A | 1/2019 |
| CN | 109199641 | A | 1/2019 |
| CN | 109561962 | A | 4/2019 |
| CN | 109567991 | A | 4/2019 |
| CN | 10986283 5 | A | 6/2019 |
| CN | 109862835 | A | 6/2019 |
| CN | 109906063 | A | 6/2019 |
| CN | 109996581 | A | 7/2019 |
| CN | 110013358 | A | 7/2019 |
| CN | 110290764 | A | 9/2019 |
| DE | 102014102648 | A1 | 9/2015 |
| DE | 102014102650 | A1 | 9/2015 |
| DE | 102014102718 | A1 | 9/2015 |
| DE | 102014102722 | A1 | 9/2015 |
| DE | 202017104793 | U1 | 11/2018 |
| DE | 202016008737 | U1 | 4/2019 |
| DK | 2549953 | T3 | 2/2017 |
| DK | 2254514 | T3 | 12/2018 |
| EA | 027348 | B1 | 7/2017 |
| EP | 0902704 | A1 | 3/1999 |
| EP | 0902704 | A4 | 3/1999 |
| EP | 1301225 | A2 | 4/2003 |
| EP | 1684666 | A2 | 8/2006 |
| EP | 1996246 | A2 | 12/2008 |
| EP | 2211779 | A1 | 8/2010 |
| EP | 2254513 | A1 | 12/2010 |
| EP | 2263605 | A1 | 12/2010 |
| EP | 2273947 | A1 | 1/2011 |
| EP | 2296744 | A1 | 3/2011 |
| EP | 2379008 | A2 | 10/2011 |
| EP | 2400926 | A2 | 1/2012 |
| EP | 2427145 | A2 | 3/2012 |
| EP | 1582178 | B1 | 9/2012 |
| EP | 2542186 | A2 | 1/2013 |
| EP | 2558030 | A1 | 2/2013 |
| EP | 2560579 | A1 | 2/2013 |
| EP | 2575681 | A1 | 4/2013 |
| EP | 2603172 | A2 | 6/2013 |
| EP | 263 7607 | A1 | 9/2013 |
| EP | 2637607 | A1 | 9/2013 |
| EP | 2651337 | A2 | 10/2013 |
| EP | 2658476 | A1 | 11/2013 |
| EP | 2699201 | A1 | 2/2014 |
| EP | 2405966 | B1 | 4/2014 |
| EP | 2055263 | B1 | 6/2014 |
| EP | 2741711 | A2 | 6/2014 |
| EP | 2793763 | A1 | 10/2014 |
| EP | 2822503 | A2 | 1/2015 |
| EP | 2538879 | B1 | 4/2015 |
| EP | 2444031 | B1 | 7/2015 |
| EP | 1702247 | B1 | 8/2015 |
| EP | 2772228 | B1 | 11/2015 |
| EP | 2943160 | A2 | 11/2015 |
| EP | 2470098 | B1 | 12/2015 |
| EP | 1991168 | B1 | 1/2016 |
| EP | 2254512 | B1 | 1/2016 |
| EP | 2964152 | A1 | 1/2016 |
| EP | 2967853 | A1 | 1/2016 |
| EP | 2967860 | A1 | 1/2016 |
| EP | 2994073 | A1 | 3/2016 |
| EP | 3001978 | A1 | 4/2016 |
| EP | 3003187 | A1 | 4/2016 |
| EP | 3007649 | A1 | 4/2016 |
| EP | 3010447 | A1 | 4/2016 |
| EP | 3017792 | A1 | 5/2016 |
| EP | 3019092 | A1 | 5/2016 |
| EP | 2563236 | B1 | 6/2016 |
| EP | 3027143 | A1 | 6/2016 |
| EP | 3037064 | A1 | 6/2016 |
| EP | 2211758 | B1 | 7/2016 |
| EP | 3052053 | A1 | 8/2016 |
| EP | 3060140 | A1 | 8/2016 |
| EP | 3062745 | A1 | 9/2016 |
| EP | 3071149 | A1 | 9/2016 |
| EP | 2282700 | B1 | 11/2016 |
| EP | 2967854 | B1 | 11/2016 |
| EP | 1998713 | | 12/2016 |
| EP | 1998713 | B1 | 12/2016 |
| EP | 3099271 | A1 | 12/2016 |
| EP | 3100701 | A1 | 12/2016 |
| EP | 3100701 | A1 | 12/2016 |
| EP | 3141219 | A1 | 3/2017 |
| EP | 3157469 | A1 | 4/2017 |
| EP | 2538880 | B1 | 5/2017 |
| EP | 2967852 | B1 | 6/2017 |
| EP | 3174503 | A1 | 6/2017 |
| EP | 3182931 | A1 | 6/2017 |
| EP | 3182931 | A1 | 6/2017 |
| EP | 2830536 | B1 | 8/2017 |
| EP | 2830537 | B1 | 9/2017 |
| EP | 2720642 | B1 | 10/2017 |
| EP | 3232941 | A1 | 10/2017 |
| EP | 3256076 | A1 | 12/2017 |
| EP | 3281608 | A1 | 2/2018 |
| EP | 2608815 | B1 | 3/2018 |
| EP | 3310302 | A1 | 4/2018 |
| EP | 3311778 | A1 | 4/2018 |
| EP | 3337412 | A1 | 6/2018 |
| EP | 3340931 | A1 | 7/2018 |
| EP | 3344188 | A1 | 7/2018 |
| EP | 3344197 | A1 | 7/2018 |
| EP | 3345573 | A1 | 7/2018 |
| EP | 2822473 | B1 | 8/2018 |
| EP | 3354208 | A1 | 8/2018 |
| EP | 3370649 | A1 | 9/2018 |
| EP | 3372198 | A1 | 9/2018 |
| EP | 3372199 | A1 | 9/2018 |
| EP | 3375411 | A1 | 9/2018 |
| EP | 2928538 | B1 | 11/2018 |

(56) References Cited

FOREIGN PATENT DOCUMENTS

| | | |
|---|---|---|
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 1301225 A4 | 8/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3508113 A1 | 10/2019 |
| EP | 3552584 A1 | 10/2019 |
| EP | 3552655 A1 | 10/2019 |
| ES | 23 69241 T3 | 11/2011 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 201422678 A | 9/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2019134972 A | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013 991 A | 2/2001 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 2014013 9060 A | 12/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2019131148 A1 | 10/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2018008019 A2 | 9/2010 |
| WO | WO-2010119110 A1 | 10/2010 |
| WO | WO-2011112706 A2 | 9/2011 |
| WO | WO-2011137531 A1 | 11/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |

(56) References Cited

FOREIGN PATENT DOCUMENTS

| | | |
|---|---|---|
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133 667 A1 | 9/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015061021 A1 | 4/2015 |
| WO | WO-2015123 607 A2 | 8/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2016148777 A1 | 9/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2019006383 A2 | 1/2018 |
| WO | WO-2018008019 A2 | 1/2018 |
| WO | WO-2018035105 A1 | 2/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018209302 A1 | 11/2018 |
| WO | WO-2018200531 A1 | 11/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-201914403 6 A1 | 7/2019 |
| WO | WO-2017161204 A1 | 7/2019 |
| WO | WO-2019131148 A1 | 7/2019 |
| WO | WO-2019136162 A1 | 7/2019 |

(56) References Cited

FOREIGN PATENT DOCUMENTS

| WO | WO-2019140293 A1 | 7/2019 |
|---|---|---|
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.
Office Action for U.S. Appl. No. 17/167,983, dated Apr. 13, 2021, 20 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 17/154,227, dated Mar. 29, 2021, 6 pages.
Office Action for U.S. Appl. No. 16/442,504, dated Jan. 14, 2020, 11 pages.
Office Action for U.S. Appl. No. 16/445,210, dated Jan. 28, 2021, 7 pages.
Office Action for U.S. Appl. No. 17/154,438, dated May 3, 2021, 16 pages.
International Search Report and Written Opinion for International Application No. PCT/US2021/013570, dated Apr. 1, 2021, 9 pages.
International Search Report and Written Opinion for International Application No. PCT/US2020/045195, dated Jan. 8, 2021, 18 pages.
Office Action for U.S. Appl. No. 17/193,936, dated May 27, 2021, 6 pages.
International Search Report and Written Opinion for International Application No. PCT/US2020/047162, dated Dec. 30, 2020, 9 pages.
Office Action for U.S. Appl. No. 16/449,420, dated Sep. 1, 2021, 16 pages.
Office Action for U.S. Appl. No. 17/154,227, dated Jun. 18, 2021, 8 pages.
Office Action for U.S. Appl. No. 17/167,988, dated Sep. 22, 2021, 19 pages.
Office Action for U.S. Appl. No. 17/221,547, dated Aug. 4, 2021, 11 pages.
Office Action for U.S. Appl. No. 17/221,547, dated Oct. 21, 2021, 9 pages.
Office Action for U.S. Appl. No. 17/222,182, dated Sep. 2, 2021, 23 pages.
Office Action for U.S. Appl. No. 17/222,430, dated Oct. 7, 2021, 17 pages.
Office Action for U.S. Appl. No. 17/236,219, dated Aug. 4, 2021, 17 pages.

* cited by examiner

FIG. 33
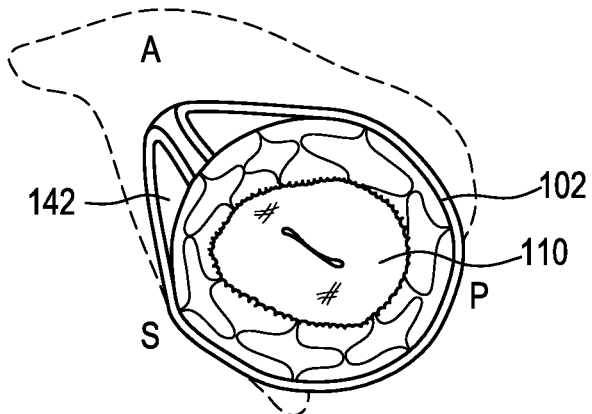
FIG. 34    FIG. 35
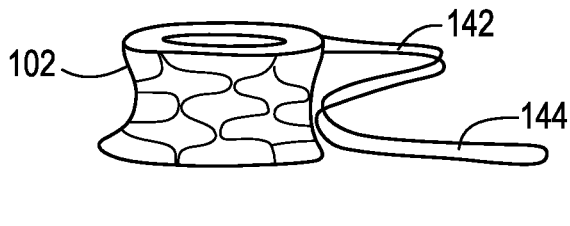   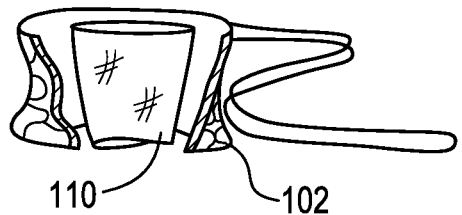
FIG. 36
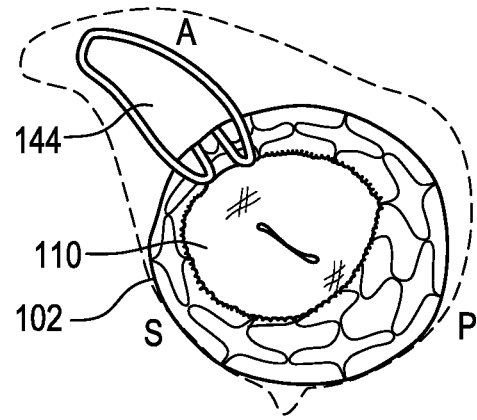

FIG. 37
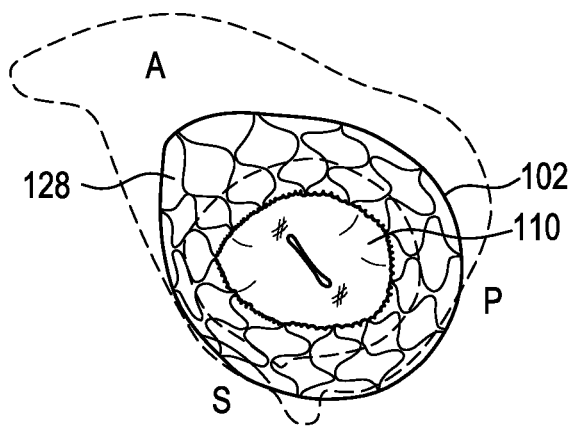
FIG. 38     FIG. 39
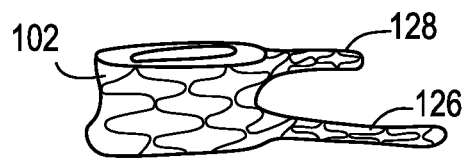 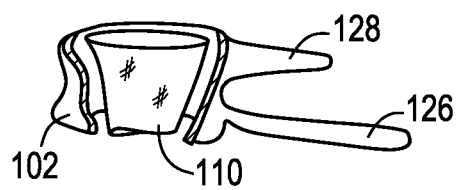
FIG. 40
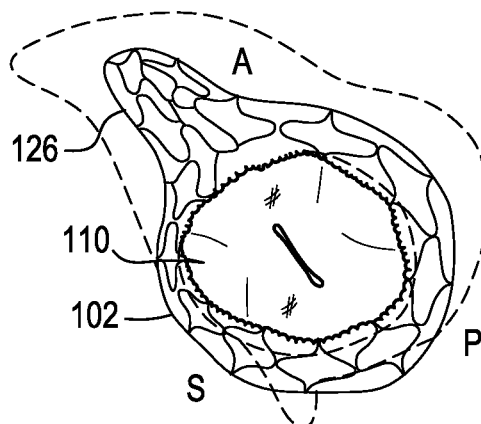

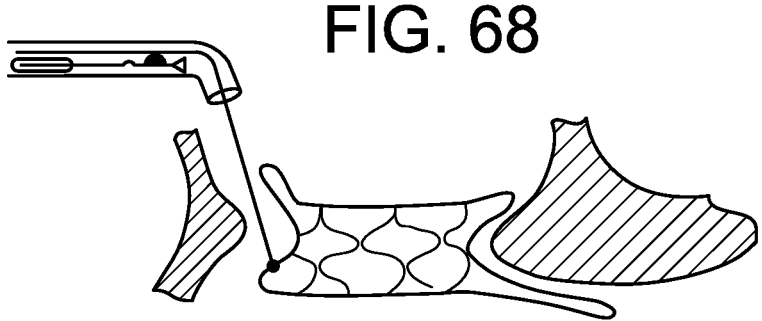
FIG. 68
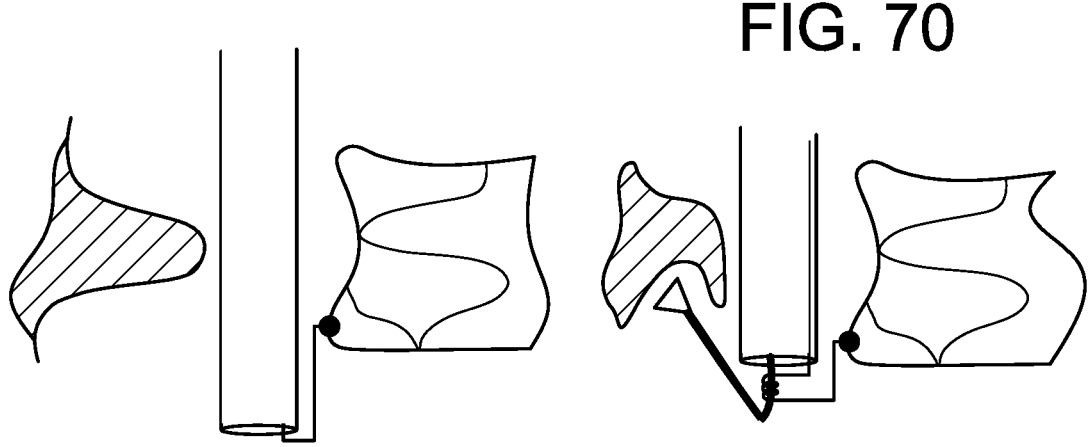
FIG. 69
FIG. 70
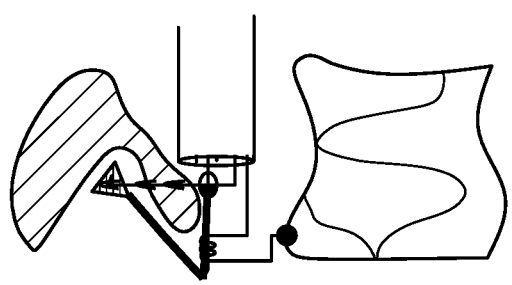
FIG. 71
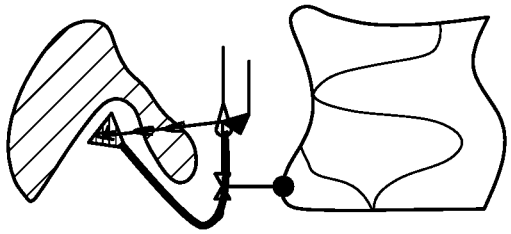
FIG. 72

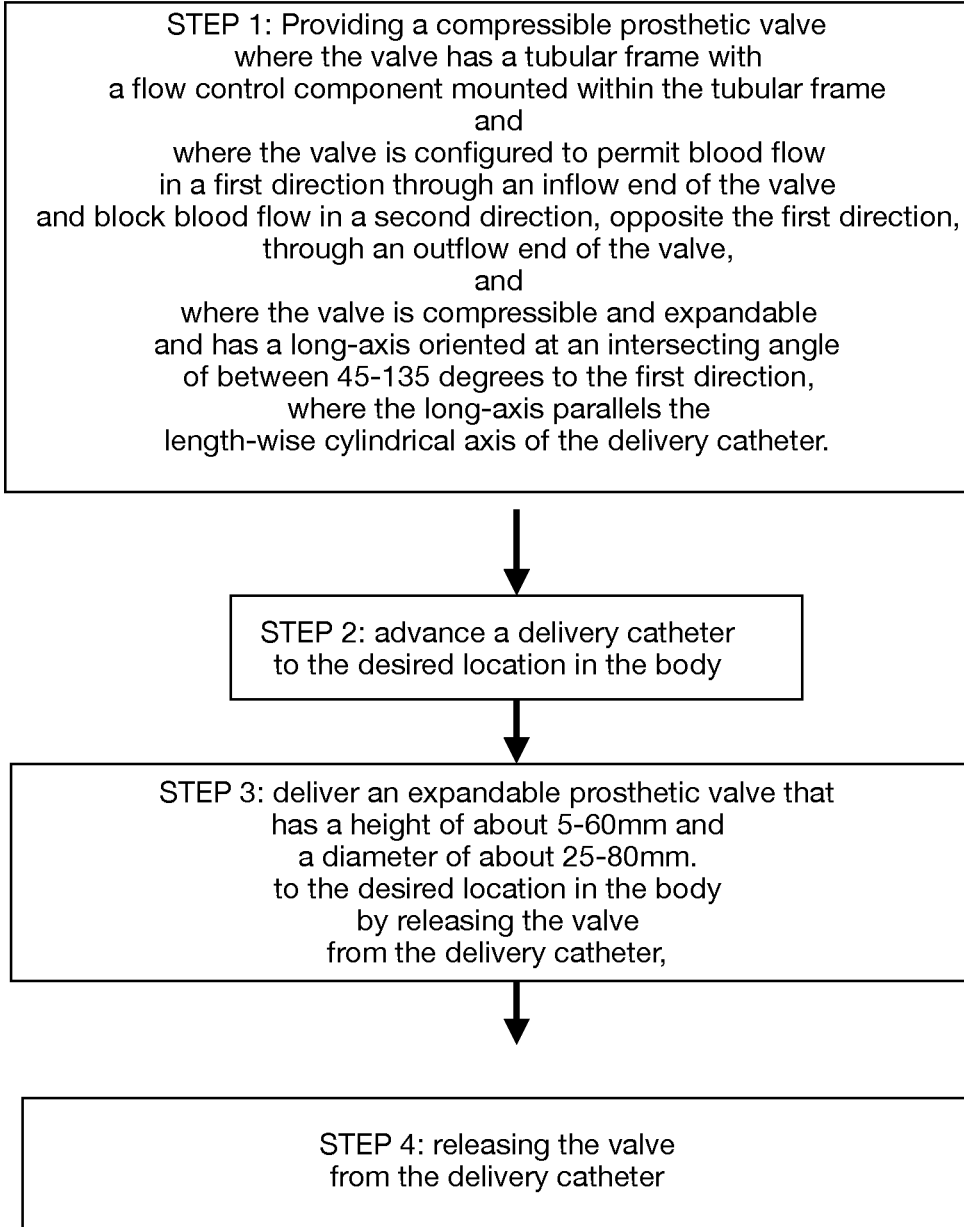

FIG. 81

Method for orthogonal delivery
of implantable prosthetic valve
to a desired location in the body STEP 1: Providing a compressible prosthetic valve
where the valve has a tubular frame with
a flow control component mounted within the tubular frame
and
where the valve is configured to permit blood flow
in a first direction through an inflow end of the valve
and block blood flow in a second direction, opposite the first direction,
through an outflow end of the valve,
and
where the valve is compressible and expandable
and has a long-axis oriented at an intersecting angle
of between 45-135 degrees to the first direction,
where the long-axis parallels the
length-wise cylindrical axis of the delivery catheter.

STEP 2: advance a delivery catheter
to the desired location in the body

STEP 3: deliver an expandable prosthetic valve that
has a height of about 5-60mm and
a diameter of about 25-80mm.
to the desired location in the body
by releasing the valve
from the delivery catheter, STEP 4: releasing the valve
from the delivery catheter

FIG. 82

Method for orthogonally loading
an implantable prosthetic valve
into a delivery catheter STEP 1: Providing a compressible prosthetic valve
where the valve has a tubular frame with
a flow control component mounted within the tubular frame
and
where the valve is configured to permit blood flow
in a first direction through an inflow end of the valve
and block blood flow in a second direction, opposite the first direction,
through an outflow end of the valve,
and
where the valve is compressible and expandable
and has a long-axis oriented at an intersecting angle
of between 45-135 degrees to the first direction,
where the long-axis parallels the
length-wise cylindrical axis of the delivery catheter
and
where the valve has
a height of about 5-60mm and
a diameter of about 25-80mm.

STEP 2: loading an implantable prosthetic valve
into a tapering fixture or funnel
attached to a delivery catheter, to a compressed configuration
for introduction into the body
using a delivery catheter
for implanting at a desired location in the body,

SIDE-DELIVERED TRANSCATHETER HEART VALVE REPLACEMENT

CROSS-REFERENCE TO RELATED APPLICATIONS

This application is a continuation of U.S. patent application Ser. No. 16/155,890 (now U.S. Pat. No. 10,321,995), filed Oct. 10, 2018, entitled "Orthogonally Delivered Transcatheter Heart Valve Replacement," which claims priority to and the benefit of U.S. Provisional Patent Application Ser. No. 62/766,611, filed Sep. 20, 2018, entitled "Side-Loading Transcatheter Heart Valve Replacement."

STATEMENT REGARDING FEDERALLY SPONSORED R&D

Provided by Application Data Sheet per USPTO rules.

The invention relates to a transcatheter heart valve replacement (A61F2/2412).

DESCRIPTION OF THE RELATED ART

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting dic technology allowed blood to flow in a more natural way while reducing damage to blood cells from mechanical forces. However, the struts of these valves tended to fracture from fatigue over time. As of 2003, more than 100,000 Omniscience and 300,000 HallKaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

Accordingly, the present invention is directed to a side delivered transcatheter prosthetic valve comprising: (i) a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter, and expandable to an expanded configuration for implanting at a desired location in the body, wherein the valve is compressible and expandable along a long-axis substantially parallel to a cylindrical axis of the delivery catheter, and wherein the valve has a height of about 5-60 mm and a diameter of about 25-80 mm.

In another preferred embodiment, there is provided a side delivered transcatheter prosthetic valve wherein the tubular frame forms a two part framework, a first part comprises a flared atrial cuff joined to a second part that comprises cylindrical member, wherein the cuff is joined to the cylindrical member around the circumference of a top edge of the cylindrical member.

In another preferred embodiment, there is provided a side delivered transcatheter prosthetic valve wherein said tubular frame is comprised of a braid, wire, or laser-cut wire frame, and said tubular frame is covered with a biocompatible material.

In another preferred embodiment, there is provided a side delivered transcatheter prosthetic valve wherein the tubular frame has a side profile of a flat cone shape having a diameter R of 40-80 mm, a diameter r of 20-40 mm, and a height of 10-20 mm.

In another preferred embodiment, there is provided a side delivered transcatheter prosthetic valve wherein the tubular frame has an inner surface and an outer surface, said inner surface covered with a biocompatible material comprising pericardial tissue, and said outer surface covered with a biocompatible material comprising a woven synthetic polyester material.

In another preferred embodiment, there is provided a side delivered transcatheter prosthetic valve wherein the tubular frame has a side profile of an hourglass flat conical shape having a top diameter R1 of 40-80 mm, a bottom diameter R2 of 50-70 mm, an internal diameter r of 20-30 mm, and a height of 5-60 mm.

In another preferred embodiment, there is provided a side delivered transcatheter prosthetic valve wherein the valve in an expanded configuration has a central tube axis that is substantially parallel to the first direction.

In another preferred embodiment, there is provided a side delivered transcatheter prosthetic valve wherein the flow control component has an internal diameter of 20-30 mm and a height of 20-40 mm, and a plurality of leaflets of pericardial material joined to form a rounded cylinder at an inflow end and having a flat closable aperture at an outflow end.

In another preferred embodiment, there is provided a side delivered transcatheter prosthetic valve wherein the flow control component is supported with one or more longitudinal supports integrated into or mounted upon the flow control component, the one or more longitudinal supports selected from rigid or semi-rigid ribs, rigid or semi-rigid battons, rigid or semi-rigid panels, and combination thereof.

In another preferred embodiment, there is provided a side delivered transcatheter prosthetic valve comprising a tension arm extending from a distal side of the tubular frame, the tension arm comprised of wire loop or wire frame extending from about 10-40 mm away from the tubular frame.

In another preferred embodiment, there is provided a side delivered transcatheter prosthetic valve comprising (i) an upper tension arm attached to a distal upper edge of the tubular frame, the upper tension arm comprised of wire loop or wire frame extending from about 2-20 mm away from the tubular frame, and (ii) a lower tension arm extending from a distal side of the tubular frame, the lower tension arm comprised of wire loop or wire frame extending from about 10-40 mm away from the tubular frame.

In another preferred embodiment, there is provided a side delivered transcatheter prosthetic valve comprising at least one tissue anchor connected to the tubular frame for engaging annular tissue.

In another preferred embodiment, there is provided a method for side delivery of implantable prosthetic valve to a desired location in the body, the method comprising the steps: (i) advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter, and expandable to an expanded configuration for implanting at a desired location in the body, wherein the valve is compressible and expandable along a long-axis substantially parallel to a cylindrical axis of the delivery catheter, wherein the valve has a height of about 5-60 mm and a diameter of about 25-80 mm.

In another preferred embodiment, there is provided a method for side delivery of implantable prosthetic valve wherein releasing the valve from the delivery catheter comprises pulling the valve out of the delivery catheter using a rigid elongated pushing rod that is releasably connected to the distal side of the valve, wherein advancing the pushing rod away from the delivery catheter pulls the compressed valve out of the delivery catheter.

In another preferred embodiment, there is provided a method for side delivery of implantable prosthetic valve comprising the additional step of anchoring one or more tissue anchors attached to the valve into annular tissue.

In another preferred embodiment, there is provided a method for side delivery of implantable prosthetic valve comprising the additional step of positioning a tension arm of the heart valve prosthesis into the right ventricular outflow tract of the right ventricle.

In another preferred embodiment, there is provided a method for side delivery of implantable prosthetic valve comprising the additional steps of positioning a lower tension arm of the heart valve prosthesis into the right ventricular outflow tract of the right ventricle, and positioning an upper tension arm into a supra-annular position, the upper tension arm connected to the lower tension arm, and the upper tension arm providing a supra-annular downward force in the direction of the ventricle and lower tension arm providing a sub-annular upward force in the direction of the atrium.

In another preferred embodiment, there is provided a method for side delivery of implantable prosthetic valve comprising the the additional step of rotating the heart valve prosthesis using a steerable catheter along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.

In another preferred embodiment, there is provided a method for side loading an implantable prosthetic valve into a delivery catheter, the method comprising the steps: (i) attaching a pulling wire to a sidewall of an implantable prosthetic valve and pulling the valve into a tapering fixture or funnel, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein pulling the valve into a tapering fixture or funnel compresses the valve to a compressed configuration for loading into a delivery catheter, wherein the valve is compressible and expandable along a long-axis substantially parallel to a cylindrical axis of the delivery catheter, wherein the valve has a height of about 5-60 mm and a diameter of about 25-80 mm.

BRIEF DESCRIPTION OF THE SEVERAL VIEWS OF DRAWING

FIG. 33 is an illustration of a TOP view of a heart valve prosthesis according to the present invention having covered wire loops for the upper tension arm(s).

FIG. 34 is an illustration of a PLAN view of a heart valve prosthesis according to the present invention having a wire loop construction for the upper and lower tension arms.

FIG. 35 is an illustration of a CUT-AWAY PLAN view of a heart valve prosthesis according to the present invention, and shows the inner panel valve sleeve mounted within the inner space defined by the tubular frame.

FIG. 36 is an illustration of a BOTTOM view of a heart valve prosthesis according to the present invention having covered wire loops for the lower tension arm.

FIG. 37 is an illustration of a TOP view of a heart valve prosthesis according to the present invention having braid or laser-cut wire frame for the upper tension arm(s).

FIG. 38 is an illustration of a PLAN view of a heart valve prosthesis according to the present invention having braid or laser-cut wire frame construction for the upper and lower tension arms.

FIG. 39 is an illustration of a CUT-AWAY PLAN view of a braid or laser-cut embodiment of the heart valve prosthesis according to the present invention, and shows the inner panel valve sleeve mounted within the inner space defined by the tubular frame.

FIG. 40 is an illustration of a BOTTOM view of a heart valve prosthesis according to the present invention having braid or laser-cut wire frame for the lower tension arm.

Figure 41:
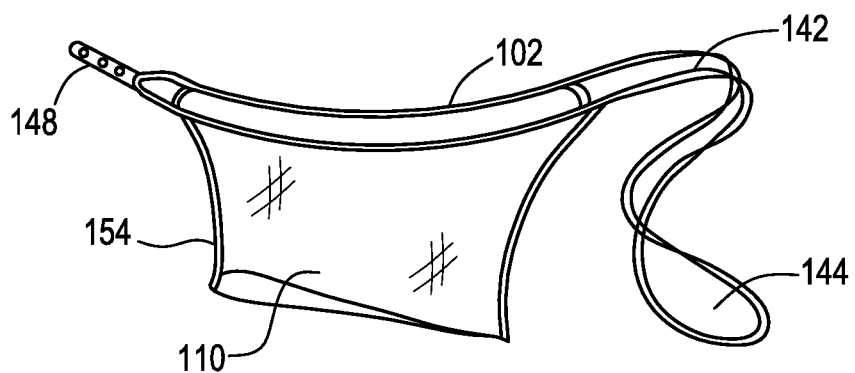

FIG. 41 is an illustration of a heart valve prosthesis according to the present invention having a wire loop construction for the tubular frame, with two vertical support posts extending down the edge on opposing sides of the valve sleeve. During compression into the delivery catheter, the posts are engineered to fold horizontally during compression, and to elastically unfold during ejection to deploy the valve sleeve.

Figure 42:
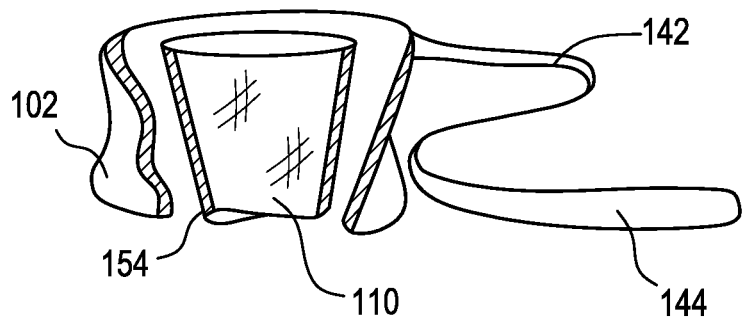

FIG. 42 is an illustration of a CUT-AWAY PLAN view of a heart valve prosthesis according to the present invention, and shows a two-post embodiment of the inner panel valve sleeve mounted within the inner space defined by the tubular frame.

Figure 43:
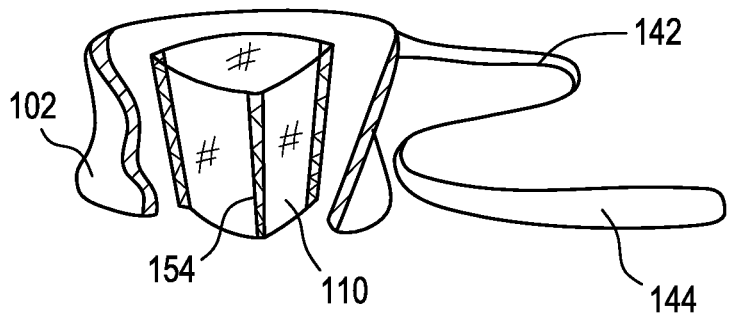

FIG. 43 is an illustration of a CUT-AWAY PLAN view of a heart valve prosthesis according to the present invention, and shows a three-panel, three-post embodiment of the inner panel valve sleeve mounted within the inner space defined by the tubular frame.

Figure 44:
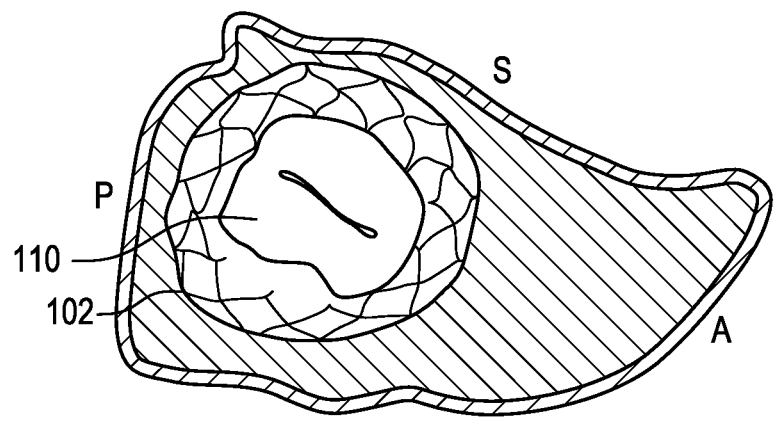

FIG. 44 is an illustration of a TOP view of a heart valve prosthesis according to the present invention having braid or laser-cut wire frame and shown mounted within a cross-sectional view of the atrial floor at the annulus.

Figure 45:
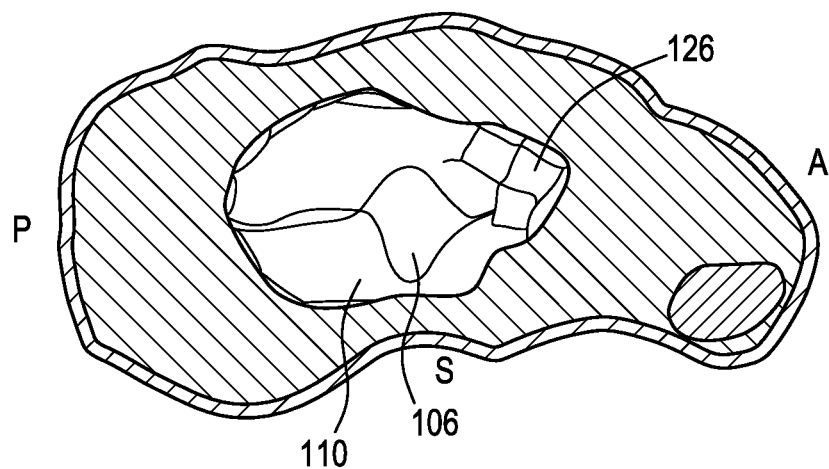

FIG. 45 is an illustration of a BOTTOM view of a heart valve prosthesis according to the present invention having braid or laser-cut wire frame for a lower tension arm and shown mounted within a cross-sectional view of the ventricular ceiling at the annulus.

Figure 46:
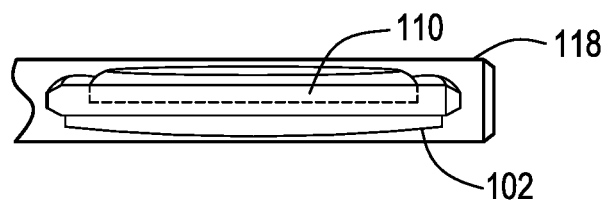

FIG. 46 is an illustration of a PLAN view of an embodiment of the prosthetic valve shown in a compressed configuration within a delivery catheter.

Figure 47:
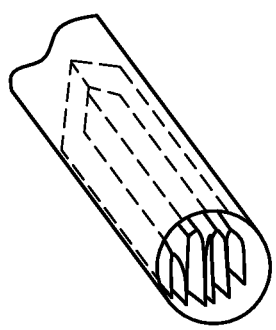

FIG. 47 is an illustration of a cross-sectional view of one embodiment of a compressed valve within a delivery catheter.

Figure 48:
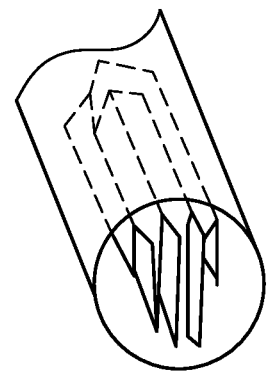

FIG. 48 is an illustration of a cross-sectional view of another embodiment of a compressed valve within a delivery catheter.

Figure 49:
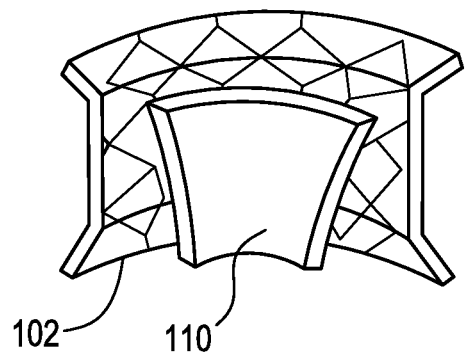

FIG. 49 is an illustration of a cross-sectional view of one embodiment of the prosthetic valve.

Figure 50A:
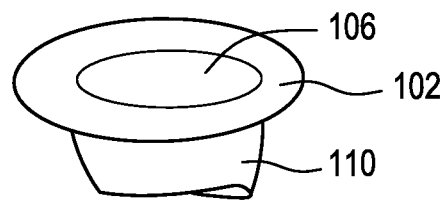
Figure 50B:
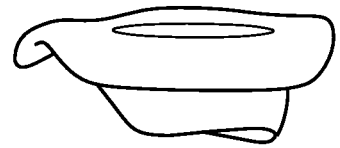
Figure 50C:

FIG. 50 (a)-(b)-(c) is an illustration of a sequence of a low-profile valve being rolled into a configuration for placement within a delivery catheter.

Figure 51:
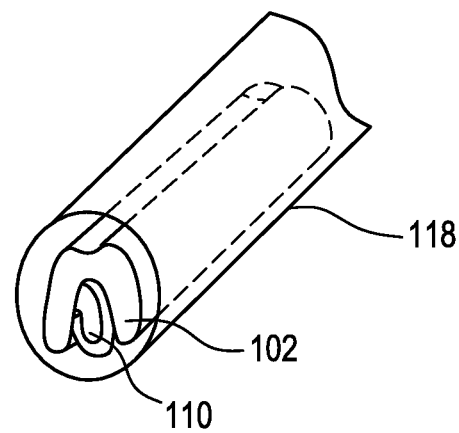

FIG. 51 is an illustration of an END-VIEW of a low-profile valve that has been longitudinally rolled and loaded within a delivery catheter.

Figure 52:
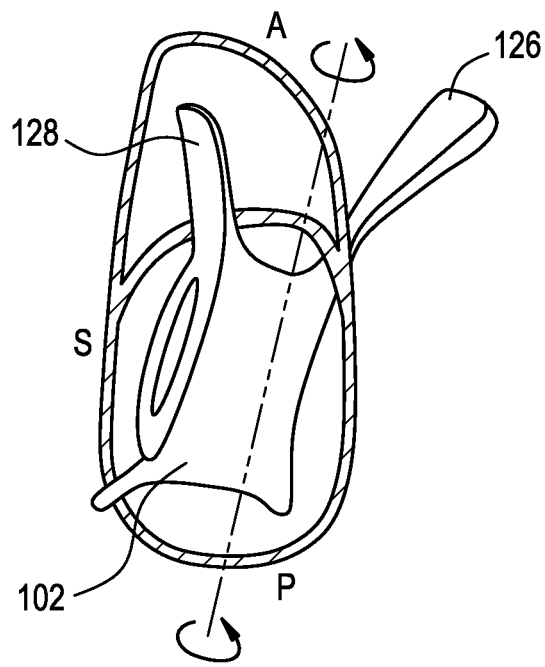

FIG. 52 is an illustration of a rotational lock embodiment of the present invention where the prosthetic valve is delivered to the native annulus with an off-set sub-annular tension arm/tab positioned below the native annulus, and an off-set supra-annular tension arm/tab positioned above the native annulus, while the tubular frame is partially rolled off-set from the annular plane along a longitudinal axis.

Figure 53:
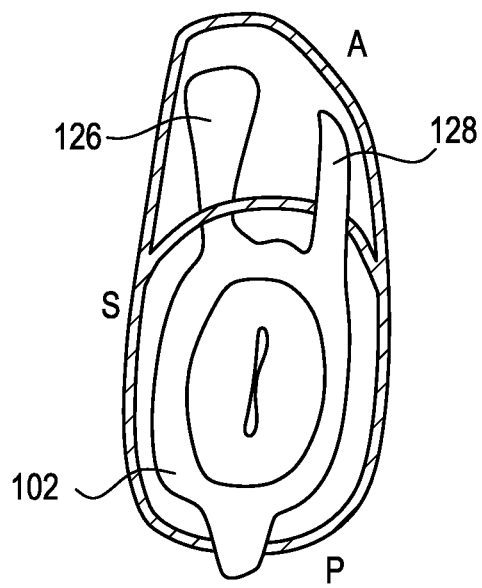

FIG. 53 is an illustration of a rotational lock embodiment of the present invention where the prosthetic valve is delivered to the native annulus with an off-set sub-annular tension arm/tab positioned below the native annulus, and an off-set supra-annular tension arm/tab positioned above the native annulus, while the tubular frame is rolled into functional position parallel to the annular plane.

Figure 54:
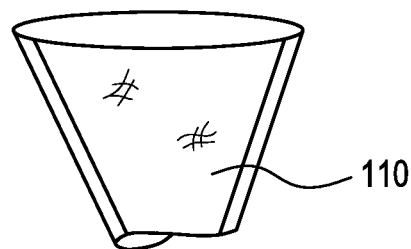

FIG. 54 is an illustration of a two-panel embodiment of an inner valve sleeve.

Figure 55:
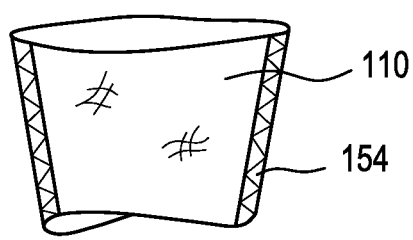

FIG. 55 is an illustration of one embodiment of an inner valve sleeve having two rigid support posts.

Figure 56:
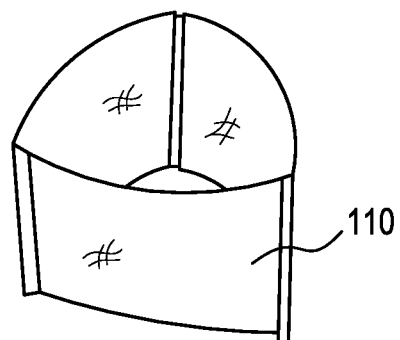

FIG. 56 is an illustration of a three-panel embodiment of an inner valve sleeve.

Figure 57:
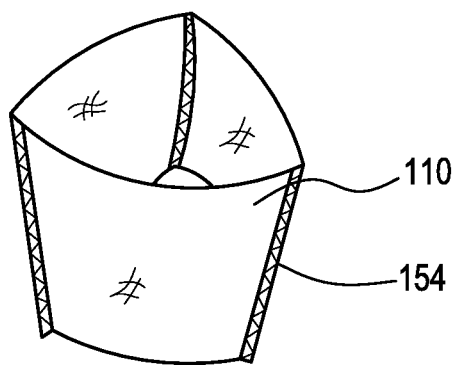

FIG. 57 is an illustration of a three-panel embodiment of an inner valve sleeve having three rigid support posts.

Figure 58:
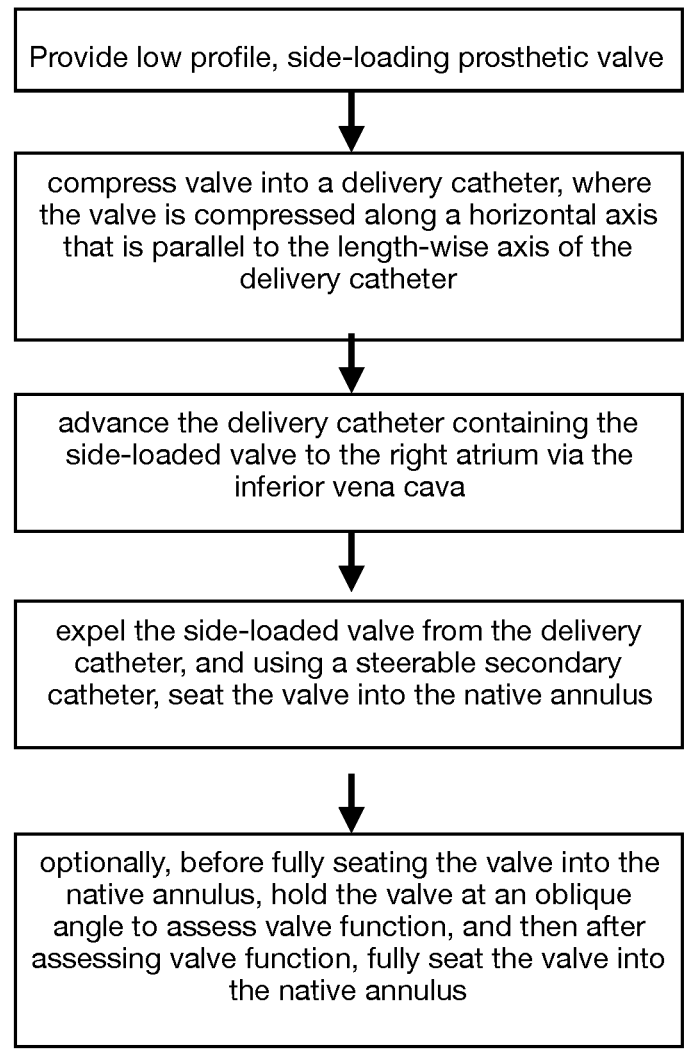

FIG. 58 is a flowchart describing one set of method steps for delivery of a low-profile, side-loaded prosthetic valve.

Figure 59A:
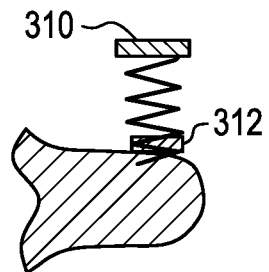
Figure 59B:
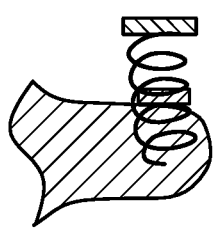
Figure 59C:
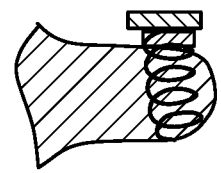

FIG. 59(a)-(c) is an illustration of a plan view of a tissue anchor having a floating radio-opaque marker. This figure shows the tissue anchor accessing the annular tissue withe the radio-opaque marker at the distal end of the anchor and in contact with the atrial surface of the annular tissue. This figure shows the tissue anchor advancing into the annular tissue with the radio-opaque marker threaded onto the tissue anchor and maintaining position on the atrial surface of the annular tissue. This figure shows the tissue anchor completely advanced into the annular tissue such that the tissue anchor and the threaded floating marker are now adjacent, indicating the desired depth, tension, and/or plication of the tissue anchor with respect to the annular tissue.

Figure 60:

FIG. 60 is an illustration of a plan view of a tissue anchor having a straight thread and a constant pitch.

Figure 61:
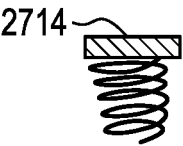

FIG. 61 is an illustration of a plan view of a tissue anchor having a straight thread and a variable pitch.

Figure 62:

FIG. 62 is an illustration of a plan view of a tissue anchor having a tapered thread and a constant pitch.

Figure 63:
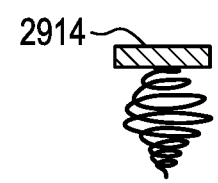

FIG. 63 is an illustration of a plan view of a tissue anchor having a sunken taper thread and a variable pitch.

Figure 64:
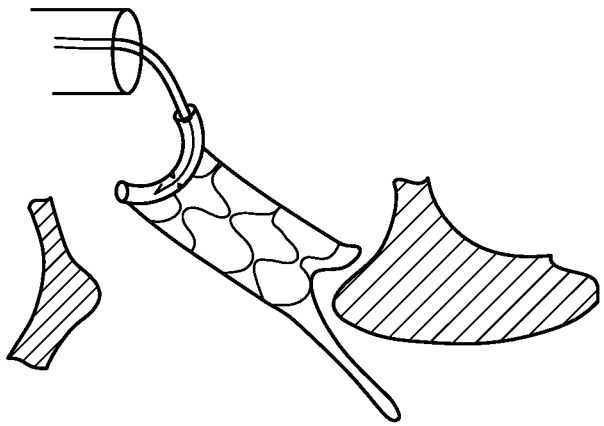

FIG. 64 is an illustration of Step 1 of a 4 step process for clipping a low profile valve to annular tissue, as shown here in a non-limiting example of clipping to a proximal or anterior side of the native annulus. FIG. 64 shows a low profile valve being inserted into the valve annulus and low profile valve having an integral anchor delivery conduit or channel with an anchor disposed in the lumen of the channel and an anchor delivery catheter attached to the anchor.

Figure 65:
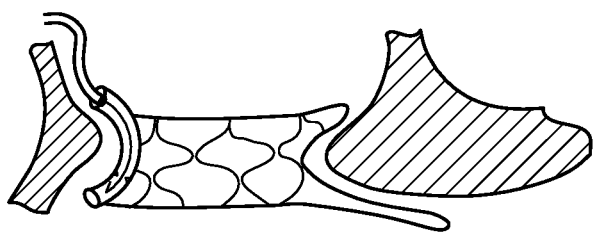

FIG. 65 is an illustration of Step 2 of a 4 step process for clipping a low profile valve to annular tissue, as shown here in a non-limiting example of clipping to a proximal or anterior side of the native annulus. FIG. 65 shows a low profile valve completely deployed within the valve annulus and an integral anchor delivery conduit or channel with an anchor disposed in the lumen of the channel and an anchor delivery catheter attached to the anchor.

Figure 66:
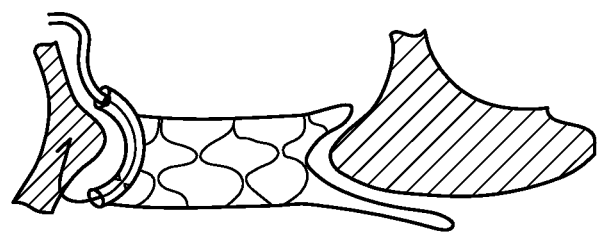

FIG. 66 is an illustration of Step 3 of a 4 step process for clipping a low profile valve to annular tissue, as shown here in a non-limiting example of clipping to a proximal or anterior side of the native annulus. FIG. 66 shows the anchor being pushed out of the lumen of the delivery conduit or channel and into the annular tissue.

Figure 67:
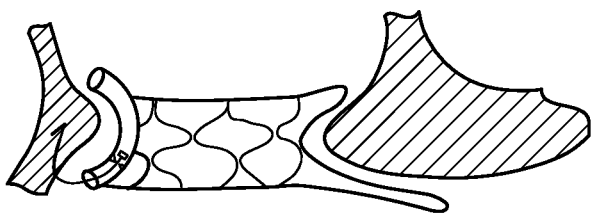

FIG. 67 is an illustration of Step 4 of a 4 step process for clipping a low profile valve to annular tissue, as shown here in a non-limiting example of clipping to a proximal or anterior side of the native annulus. FIG. 67 shows the anchor in a locked position after being pushed out of the lumen of the delivery conduit or channel and into the annular tissue, thus anchoring the proximal side of the low profile valve.

FIG. 68 is an illustration of Step 1 of a 5 step process for clipping a low profile valve to annular tissue, as shown here in a non-limiting example of clipping to a proximal or anterior side of the native annulus. FIG. 68 shows catheter delivery of an attachment wire with the clip housed within the lumen of the clip delivery catheter.

FIG. 69 is an illustration of Step 2 of a 5 step process for clipping a low profile valve to annular tissue, as shown here in a non-limiting example of clipping to a proximal or anterior side of the native annulus. FIG. 69 shows the clip delivery catheter inserted into an intra-annular space and shows an attachment wire and shows the clip housed within the lumen of the clip delivery catheter.

FIG. 70 is an illustration of Step 3 of a 5 step process for clipping a low profile valve to annular tissue, as shown here in a non-limiting example of clipping to a proximal or anterior side of the native annulus. FIG. 70 shows a receiver element ejected from the delivery catheter and positioned behind tissue to be captured.

FIG. 71 is an illustration of Step 4 of a 5 step process for clipping a low profile valve to annular tissue, as shown here in a non-limiting example of clipping to a proximal or anterior side of the native annulus. FIG. 71 shows an anchor element piercing the annular tissue and inserting into a receiver element.

FIG. 72 is an illustration of Step 5 of a 5 step process for clipping a low profile valve to annular tissue, as shown here in a non-limiting example of clipping to a proximal or anterior side of the native annulus. FIG. 72 shows that the clip delivery catheter is withdrawn and the anchor element and receiver element are connected to the annular tissue and a also connected by connector wire to the low profile valve.

Figure 73:
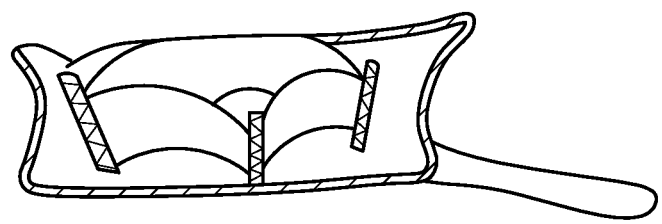

FIG. 73 is an illustration of one embodiment of a partial cut-away interior view of a tri-leaflet embodiment of a low-profile, e.g. 8-20 mm, side-loaded prosthetic valve.

Figure 74:
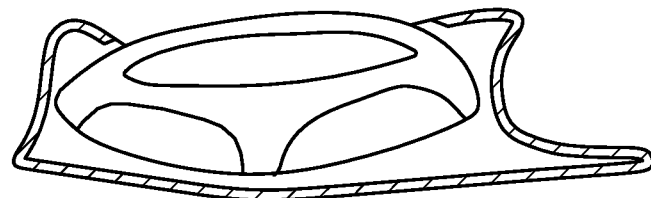

FIG. 74 is an illustration of another embodiment of a partial cut-away interior view of a tri-leaflet embodiment of a low-profile, e.g. 8-20 mm, side-loaded prosthetic valve.

Figure 75:
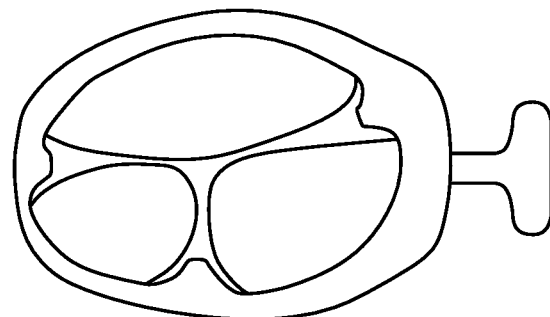

FIG. 75 is an illustration of a top view of a tri-leaflet embodiment of a low-profile, e.g. 8-20 mm, side-loaded prosthetic valve.

Figure 76:
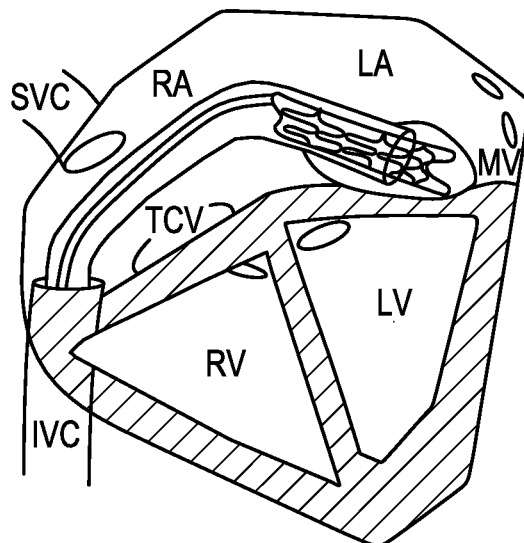

FIG. 76 is an illustration of the trans-septal (femoral-IVC) delivery of a low-profile, e.g. 8-20 mm, side-loaded prosthetic MITRAL valve shown partially housed within the delivery catheter, and partially ejected for deployment into the native mitral annulus.

Figure 77:
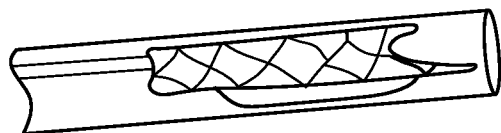

FIG. 77 is an illustration of a low-profile, e.g. 8-20 mm, side-loaded prosthetic MITRAL valve shown housed within the delivery catheter.

Figure 78:
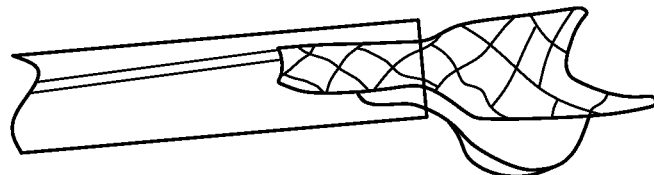

FIG. 78 is an illustration of a low-profile, e.g. 8-20 mm, side-loaded prosthetic MITRAL valve shown partially housed within a delivery catheter and partially latterally ejected from the delivery catheter and positioned for deployment against the anterior side of the native mitral annulus.

Figure 79:
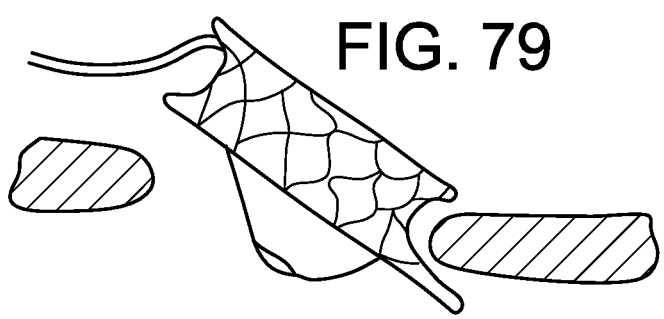

FIG. 79 is an illustration of a low-profile, e.g. 8-20 mm, side-loaded prosthetic MITRAL valve shown ejected from the delivery catheter and positioned against the anterior side of the native mitral annulus.

Figure 80:
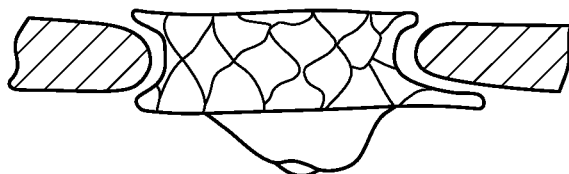

FIG. 80 is an illustration of a side or plan view of a low-profile, e.g. 8-20 mm, side-loaded prosthetic valve shown deployed into the native MITRAL annulus.

FIG. 81 is a flowchart showing a preferred embodiment of a method for side delivery of implantable prosthetic valve to a desired location in the body.

FIG. 82 is a flowchart showing a preferred embodiment of a method for side loading of an implantable prosthetic valve into a delivery catheter.

FIG. 83(*a*)-(*d*) is an illustration of one embodiment of the invention showing a four step (a)-(d) process for compressing a prosthetic valve to provide a long-axis that is coplanar or parallel with the length-wise axis of a delivery catheter.

DETAILED DESCRIPTION OF THE INVENTION

The invention is directed to a transcatheter heart valve replacement that is a low profile, side delivered implantable prosthetic valve having an ring-shaped tubular frame, an inner 2- or 3-panel sleeve, an elongated sub-annular tension arm extending into the right ventricular outflow tract, and one or more anchor elements.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Side Delivery or Orthogonal Delivery

In the description and claims herein, the term "side" or "orthogonal" is used to describe that the valves of the present invention are compressed and delivered at a roughly 90 degree angle compared to traditional transcatheter heart valves. Traditional valves have a central cylinder axis that is parallel to the length-wise axis of the delivery catheter and are deployed from the end of the delivery catheter in a manner akin to pushing a closed umbrella out of a sleeve. The valves of the present invention are compressed and delivered in a sideways manner. Traditional valves can only be expanded as large as what the internal diameter of the delivery catheter will allow. Efforts to increase the expanded diameter of traditional valves have run into the problems of trying to compress too much material and structure into too little space. Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic valve where the blood is flowing, eg. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

Tubular Frame

In the description and claims herein, the term "tubular frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

Tubular Frame Structure

The tubular frame can be a ring, or cylindrical or conical tube, made from a durable, biocompatible structural material such as Nitinol or similar alloy, wherein the tubular frame is formed by manufacturing the structural material as a braided wire frame, a laser-cut wire frame, or a wire loop. The tubular frame is about 5-60 mm in height, has an outer diameter dimension, R, of 30-80 mm, and an inner diameter dimension of 31-79 mm, accounting for the thickness of the wire material itself. As stated, the tubular frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In one preferred embodiment, the tubular frame used in the prosthetic valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic valve may start in a roughly tubular configuration (centric or radially symmetrical), and be heat-shaped to provide an upper atrial cuff or flange for atrial sealing and a lower trans-annular tubular section that conforms to the native annulus (eccentric or radially asymmetrical) such as an example having an hourglass cross-section for about 60-80% of the circumference to conform to the native annulus along the posterior and anterior annular segments while remaining substantially vertically flat along 20-40% of the annular circumference to conform to the septal annular segment.

Tubular Frame Covering

The tubular frame is optionally internally or externally covered, partially or completely, with a biocompatible material such as pericardium. The tubular frame may also be optionally externally covered, partially or completely, with a second biocompatible material such as polyester or Dacron®.

Tubular Frame Purpose

The tubular frame has a central axial lumen where a prosthetic valve or flow-control structure, such as a reciprocating compressible sleeve, is mounted across the diameter of the lumen. The tubular frame is also tensioned against the inner aspect of the native annulus and provides structural patency to a weakened annular ring.

Tubular Frame Optional Collars

The tubular frame may optionally have a separate atrial collar attached to the upper (atrial) edge of the frame, for deploying on the atrial floor, that is used to direct blood from the atrium into the sleeve and to seal against blood leakage around the tubular frame. The tubular frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Tubular Frame Delivery

The tubular frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic valves having either a single atrial collar, a single ventricular collar, or having no additional collar structure.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a tubular frame, to function as a prosthetic valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of -, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution

Ejection fraction is a measurement of the percentage of blood leaving your heart each time it contracts. During each heartbeat pumping cycle, the heart contracts and relaxes. When your heart contracts, it ejects blood from the two pumping chambers (ventricles)

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Frame Material

Preferably, the frame is made from superelastic metal wire, such as Nitinol™ wire or other similarly functioning material. The material may be used for the frame/stent, for the collar, and/or for anchors. It is contemplated as within the scope of the invention to use other shape memory alloys such as Cu—Zn—Al—Ni alloys, Cu— Al—Ni alloys, as well as polymer composites including composites containing carbon nanotubes, carbon fibers, metal fibers, glass fibers, and polymer fibers. It is contemplated that the frame may be constructed as a braid, wire, or laser cut wire frame. Such materials are available from any number of commercial manufacturers, such as Pulse Systems. Laser cut wire frames are preferably made from Nickel-Titanium (Nitinol™), but also without limitation made from stainless steel, cobalt chromium, titanium, and other functionally equivalent metals and alloys, or Pulse Systems braided frame that is shape-set by heat treating on a fixture or mandrel.

One key aspect of the frame design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required compression features.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is placed on a mold of the desired shape, heated to the Martensitic temperature and quenched. The treatment of the wire frame in this manner will form a device that has shape memory properties and will readily revert to the memory shape at the calibrated temperature.

Braided Wire

A frame can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided wire frame is placed on a shaping fixture and placed in a muffle furnace at a specified temperature to set the wire frame to the desired shape and to develop the martensitic or super elastic properties desired.

Tethers—The tethers are made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines-Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic valve may or may not include a ventricular collar, the anchor or dart is not attached to a lower ventricular collar, but is attached directly into annular tissue or other tissue useful for anchoring.

Tube and/or Cover Material—Biological Tissue

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. *Taxus* (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

Example

One preferred embodiment of a side delivered transcatheter prosthetic valve has a tubular frame with a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm. Importantly, this heart valve substitute does not have a traditional valve configuration, can be delivered to the heart using the inferior vena cava (IVC/femoral transcatheter delivery pathway compressed within a catheter, and expelled from the catheter to be deployed without open heart surgery.

Example

In another preferred embodiment of a transcatheter valve, comprises: a cylindrical tubular frame having a height of about 5-60 mm and an outer diameter of about 25-80 mm, said tubular frame comprised of a braid, wire, or laser-cut wire frame having a substantially circular central aperture, said tubular frame partially covered with a biocompatible material; a collapsible flow control component disposed within the central aperture, said sleeve having a height of about 5-60 mm and comprised of at least two opposing leaflets that provide a reciprocating closable channel from a heart atrium to a heart ventricle; an upper tension arm attached to a distal upper edge of the tubular frame, the upper tension arm comprised of stent, segment of tubular frame, wire loop or wire frame extending from about 10-30 mm away from the tubular frame; a lower tension arm extending from a distal side of the tubular frame, the lower tension arm comprised of stent, segment of tubular frame, wire loop or wire frame extending from about 10-40 mm away from the tubular frame; and at least one tissue anchor to connect the tubular frame to native tissue.

Example

In another preferred embodiment of a transcatheter valve, there is provided a feature wherein the sleeve is shaped as a conic cylinder, said top end having a diameter of 30-35 mm and said bottom end having a diameter of 8-20 mm.

Example

In another preferred embodiment of a transcatheter valve, there is provided a feature wherein the cover is comprised of polyester, polyethylene terephthalate, decellularized pericardium, or a layered combination thereof.

Example

In a preferred embodiment of the invention, there is also provided a method for side delivery of implantable prosthetic valve to a desired location in the body, the method comprising the steps: (i) advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

Example

In a preferred embodiment of the invention, there is also provided a method for loading an implantable prosthetic valve into a delivery catheter, the method comprising the steps: loading an implantable prosthetic valve sideways into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

Example

In a preferred embodiment of the invention, there is also provided a method for loading an implantable prosthetic valve into a delivery catheter, the method comprising the steps: (i) loading an implantable prosthetic valve into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

Example

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis. The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound, and in a preferred embodiment the valve self-expands upon release from the catheter since it is constructed in part from shape-memory material, such as Nitinol®, a nickel-titanium alloy used in biomedical implants.

In another embodiment, the valve may be constructed of materials that requires balloonexpansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Drawings

Figure 1:
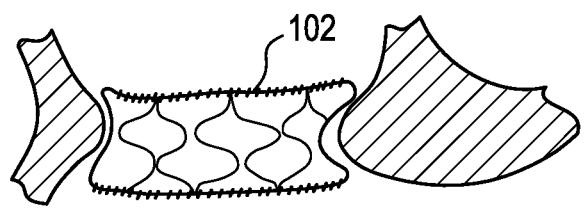
FIG. 1 is an illustration of a low-profile, e.g. 8-20 mm, side-loaded prosthetic valve shown deployed into the native annulus.

Referring now to the drawings, FIG. 1 is an illustration of a low-profile, e.g. 8-20 mm, side-loaded prosthetic valve shown deployed into the native annulus. FIG. 1 shows that low-profile, side-loaded valves can be delivered and traditionally anchored without the need for shaped, tension arms.

Figure 2:
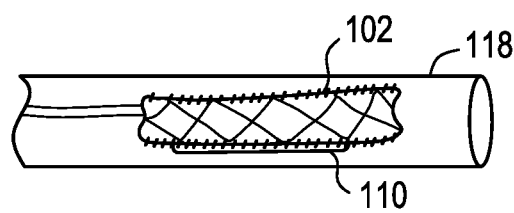
FIG. 2 is an illustration of a low-profile, e.g. 8-20 mm, side-loaded prosthetic valve shown compressed or housed within the delivery catheter.

FIG. 2 is an illustration of a low-profile, e.g. 8-20 mm, side-loaded prosthetic valve having frame 102 and sleeve 110 shown compressed or housed within the delivery catheter 118.

Figure 3:
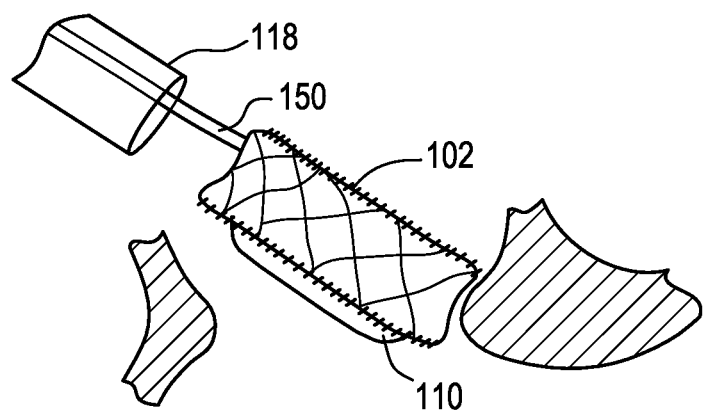
FIG. 3 is an illustration of a low-profile, e.g. 8-20 mm, side-loaded prosthetic valve shown ejected from the delivery catheter and positioned against the anterior side of the native annulus.

FIG. 3 is an illustration of a low-profile, e.g. 8-20 mm, side-loaded prosthetic valve shown ejected from the delivery catheter 118 and positioned against the anterior side of the native annulus. While the valve is held at this oblique angle by secondary catheter 150, valve function and patient condition are assessed, and if appropriate the valve is completely deployed within the native annulus, and anchored using traditional anchoring elements.

Figure 4:
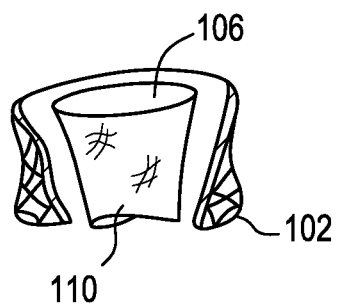
FIG. 4 is an illustration of a open cross-section view of a low-profile, side-loaded prosthetic valve and shows the inner valve sleeve.

FIG. 4 is an illustration of an open cross-section view of a low-profile, side-loaded prosthetic valve and shows the inner valve sleeve 110 and frame 102.

Figure 5:
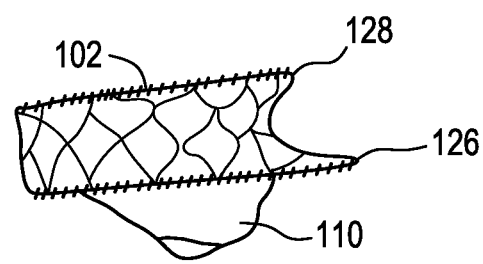
FIG. 5 is an illustration of a heart valve prosthesis according to the present invention having a braid or laser-cut construction for the tubular frame, with a valve sleeve that extends beyond the bottom of the tubular frame.

FIG. 5 is an illustration of a low-profile, side-loaded heart valve prosthesis according to the present invention having a braid or laser-cut construction for the tubular frame 102, with a valve sleeve 110 that extends beyond the bottom of the tubular frame. FIG. 5 shows a longer lower tension arm 126 for extending sub-annularly towards the RVOT, and a shorter upper tension arm 128 for extending over the atrial floor. FIG. 5 shows an elongated two (2) panel valve sleeve 110 that extends into the sub-annular leaflet space. The tubular frame 102 shown in FIG. 5 is about 10 mm in height and the valve sleeve 110 extends about 10 mm below the bottom of the tubular frame, resulting in a valve 20 mm in total height.

Figure 6:
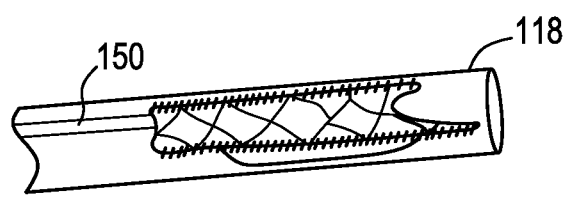
FIG. 6 is an illustration of a heart valve prosthesis having a braid or laser-cut tubular frame and extended valve sleeve compressed within a delivery catheter.

FIG. 6 is an illustration of a low-profile, side-loaded heart valve prosthesis having a braid or laser-cut tubular frame and extended valve sleeve compressed within a delivery catheter 118. FIG. 6 shows the valve attached to a secondary steerable catheter 150 for ejecting, positioning, and anchoring the valve. The secondary catheter 150 can also be used to retrieve a failed deployment of a valve.

Figure 7:
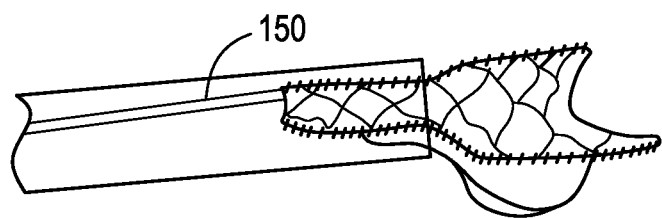
FIG. 7 is an illustration of a heart valve prosthesis having a braid or laser-cut tubular frame and extended valve sleeve shown partially compressed within a delivery catheter, and partially ejected from the delivery catheter.

FIG. 7 is an illustration of a heart valve prosthesis having a braid or laser-cut tubular frame and extended valve sleeve shown partially compressed within a delivery catheter, and partially ejected from the delivery catheter. FIG. 7 shows that while the valve is still compressed the lower tension arm can be manipulated through the leaflets and chordae tendinae to find a stable anterior-side lodgment for the distal side of the valve.

Figure 8:
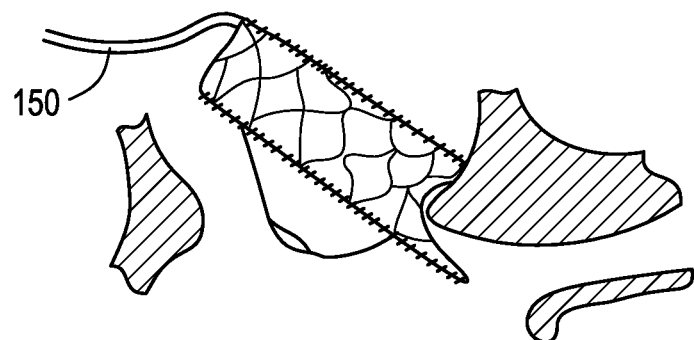
FIG. 8 is an illustration of a heart valve prosthesis having a braid or laser-cut tubular frame and extended valve sleeve engaging the tissue on the anterior side of the native annulus with the curved distal side-wall of the tubular frame sealing around the native annulus.

FIG. 8 is an illustration of a heart valve prosthesis having a braid or laser-cut tubular frame and extended valve sleeve engaging the tissue on the anterior side of the native annulus with the curved distal side-wall of the tubular frame sealing around the native annulus. FIG. 8 shows the valve held by the steerable secondary catheter at an oblique angle while valve function is assessed.

Figure 9:
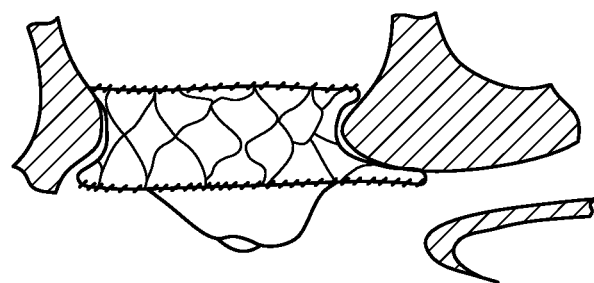
FIG. 9 is an illustration of a heart valve prosthesis having a braid or laser-cut tubular frame and extended valve sleeve engaging the tissue on the anterior side of the native annulus with the curved distal side-wall of the tubular frame sealing around the native annulus, and with the proximal side-wall tension-mounted into the posterior side of the native annulus.

FIG. 9 is an illustration of a heart valve prosthesis having a braid or laser-cut tubular frame and extended valve sleeve fully deployed into the tricuspid annulus. The distal side of the valve is shown engaging the tissue on the anterior side of the native annulus with the curved distal side-wall of the tubular frame sealing around the native annulus, and with the proximal side-wall tension-mounted into the posterior side of the native annulus.

Figure 10:
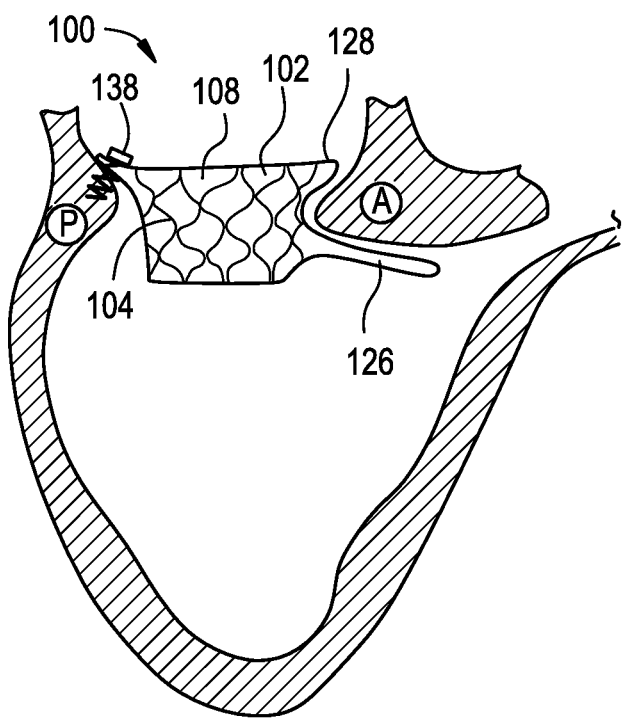
FIG. 10 is an illustration of a plan view of a heart valve prosthesis according to the present invention with a valve frame having a distal upper and lower tension arm mounted on, and anchored to, the anterior leaflet side of the native annulus, and having a mechanical anchor element, e.g. surgical tissue screw, anchored on a posterior or septal side of the native annulus.

FIG. 10 is an illustration of a plan view of a heart valve prosthesis 100 according to the present invention with a valve frame 102 having upper tension arm 128 and lower tension arm 126 mounted on and anchoring to the annulus. FIG. 10 shows lower tension arm/tab 126 extending into the Right Ventricular Outflow Tract (RVOT). The lateral, or side-loaded, delivery of the valve 100 through the inferior vena cava, provides for direct access to the valve annulus without the need to delivery a compressed valve around a right angle turn, as is required for IVC delivery of axially, or vertically loaded, traditional transcatheter valves. FIG. 10 shows one embodiment where a screw or other anchor device 138 is used in conjunction with the tension-mounting method described herein where upper and lower tension arms on the anterior leaflet side anchor the valve in place, and a secondary anchor element completes the securement of the valve in the annular site.

Figure 11:
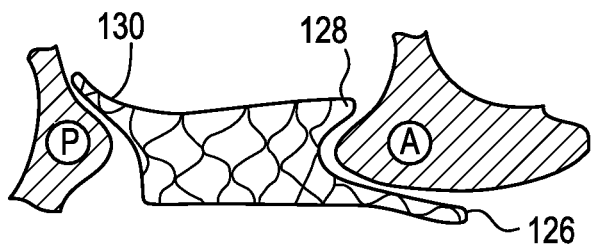
FIG. 11 is an illustration of a plan view of a heart valve prosthesis according to the present invention with a valve frame having a distal upper and lower tension arm mounted on, and anchored to, the anterior leaflet side of the native annulus, and having a mechanical anchor element, e.g. proximal sealing cuff, for anchoring on the posterior and septal side of the native annulus.

FIG. 10 shows polyester mesh covering 108 a valve tubular frame 102 encircling a collapsible flow control sleeve 110. FIG. 11 also shows the frame 102 having Nitinol wire frame in diamond shapes with a biocompatible covering. In one embodiment, the frame may have a pericardial material on top and a polyester material, e.g. surgical Dacron®, underneath to be in contact with the native annulus and promote in-growth.

FIG. 11 is an illustration of a plan view of another embodiment of a heart valve prosthesis according to the present invention with a valve frame 102 having a distal upper tension arm 128 and lower tension arm 126 mounted on, and anchored to, the anterior leaflet side of the native annulus, and having a mechanical anchor element, e.g. proximal sealing cuff, 130 for anchoring on the posterior and septal side of the native annulus. The sealing cuff 130 may be a short tab on the posterior side of the valve or may be a semi-circular or circular collar or cuff that engages the atrial floor to seal the annulus from perivalvular leaks.

Figure 12:
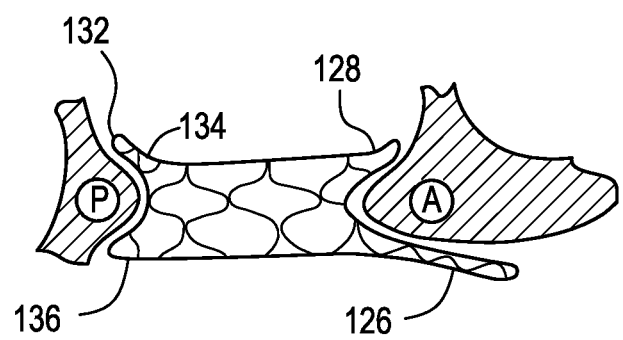
FIG. 12 is an illustration of a plan view of a heart valve prosthesis according to the present invention with a valve frame having a distal upper and lower tension arm mounted on, and anchored to, the anterior leaflet side of the native annulus, and having a mechanical anchor element, e.g. hourglass annular seal, for anchoring on the posterior and/or septal side of the native annulus.

FIG. 12 is an illustration of a plan view of another embodiment of a heart valve prosthesis according to the present invention with a valve frame having a distal upper and lower tension arm mounted on, and anchored to, the anterior leaflet side of the native annulus, and having a mechanical anchor element, e.g. hourglass annular seal, 132 for anchoring on the posterior and/or septal side of the native annulus. The hourglass, or concave, sealing cuff 132 may be only a short segment on the posterior side of the valve or may be a semi-circular or circular combined upper and lower collar or cuff that engages the atrial floor and the ventricular ceiling to seal the annulus from perivalvular leaks. This embodiment may also include embodiments having a partial collar. This embodiment may be used in conjunction with other anchoring elements described herein.

Figure 13:
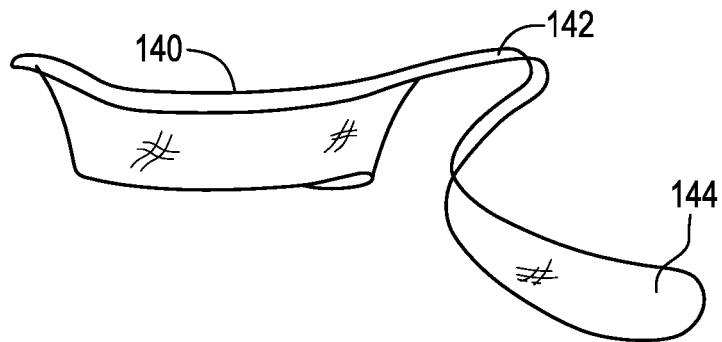
FIG. 13 is an illustration of a PLAN view of a low-profile, e.g. 10 mm in height, wire loop embodiment of the heart valve prosthesis having an annulus support loop and an upper and lower tension arm formed as a unitary or integral part, and covered with a biocompatible material.

FIG. 13 is an illustration of a PLAN view of a low-profile, e.g. 10 mm in height, wire loop embodiment of the heart valve prosthesis having an annulus support loop 140 and an upper and lower tension arm 142, 144 formed as a unitary or integral part, and covered with a biocompatible material. This embodiment shows how a low profile, side-loaded valve can having a very large diameter, 40-80 mm, with requiring an excessively large delivery catheter, as would be required by a large diameter valve that is delivered using the traditional, vertical or axial, orientation.

Figure 14:
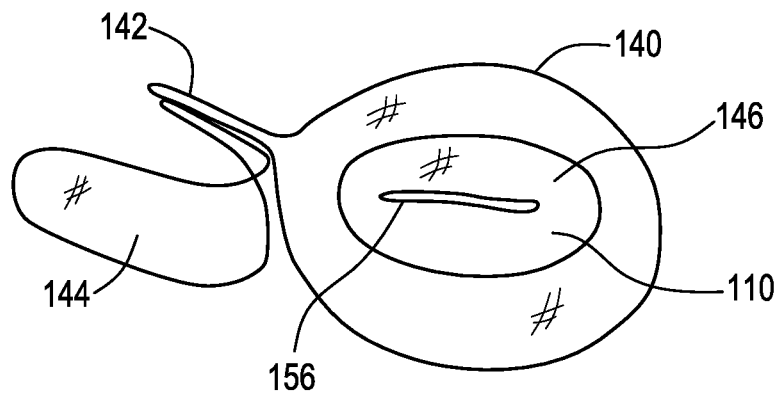
FIG. 14 is an illustration of a TOP view of a low-profile, e.g. 10 mm in height, wire loop embodiment of the heart valve prosthesis having an annulus support loop, an upper and lower tension arm formed as a unitary or integral part, an inner two-panel conical valve sleeve, and covered with a biocompatible material.

FIG. 14 is an illustration of a TOP view of a low-profile, e.g. 10 mm in height, wire loop embodiment of the heart valve prosthesis having an annulus support loop 140, an upper and lower tension arm 142, 144 formed as a unitary or integral part, an inner two-panel conical valve sleeve 110, and covered with a biocompatible material. FIG. 14 shows the inner two-panel sleeve and the reciprocating collapsible aperture at the lower end for delivering blood to the ventricle.

Figure 15:
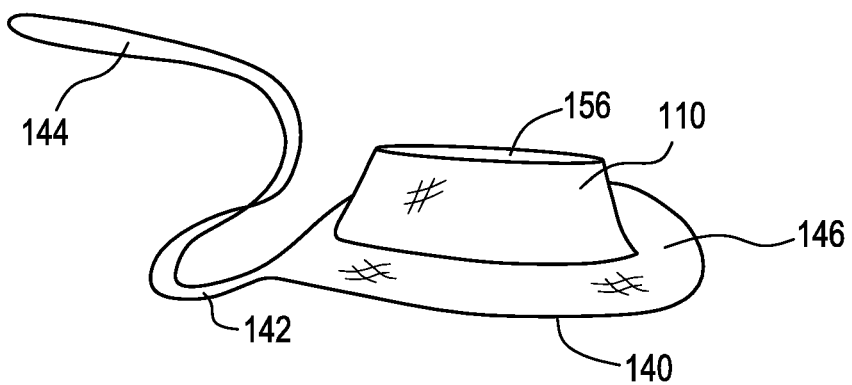
FIG. 15 is an illustration of a BOTTOM view of a low-profile, e.g. 10 mm in height, wire loop embodiment of the heart valve prosthesis having an annulus support loop, an upper and lower tension arm formed as a unitary or integral part, an inner two-panel conical valve sleeve, and covered with a biocompatible material.

FIG. 15 is an illustration of a BOTTOM view of a low-profile, e.g. 10 mm in height, wire loop embodiment of the heart valve prosthesis having an annulus support loop, an upper and lower tension arm formed as a unitary or integral part, an inner two-panel conical valve sleeve, and covered with a biocompatible material. FIG. 15 shows a PLAN view of the inner two-panel sleeve 110 and the collapsible terminal aperture 156 at the ventricular side.

Figure 16:
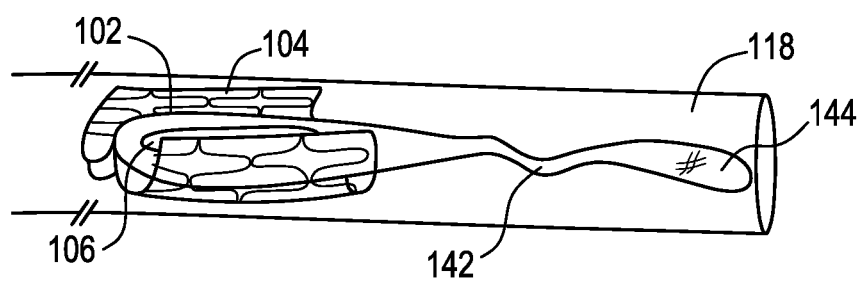
FIG. 16 is an illustration of a compressed and elongated wire loop embodiment of the heart valve prosthesis disposed within a delivery catheter and having an annulus support loop and an upper and lower tension arm formed as a unitary or integral part.

FIG. 16 is an illustration of a compressed and elongated wire loop embodiment of the heart valve prosthesis disposed within a delivery catheter 118 and having an ring shaped tubular frame 102 with braid/laser-cut 104 and an upper and lower tension arm 142, 144 formed as a unitary or integral part. FIG. 16 illustrates how a large diameter valve, using side-loading, can be delivered.

Figure 17:
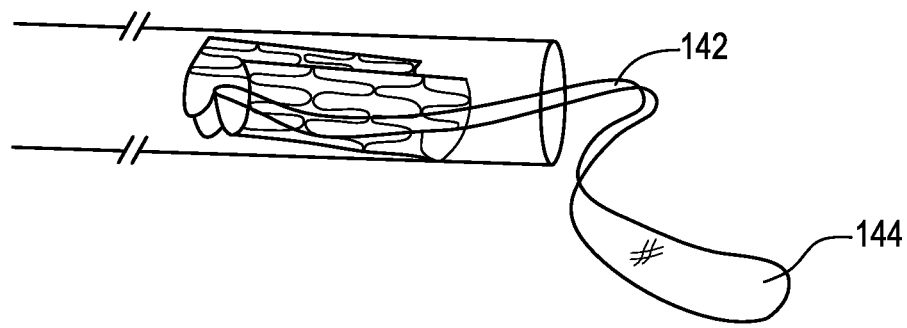
FIG. 17 is an illustration of a compressed and elongated wire loop embodiment of the heart valve prosthesis partially ejected, and partially disposed within, a delivery catheter and having an annulus support loop and an upper and lower tension arm formed as a unitary or integral part.

FIG. 17 is an illustration of a compressed and elongated wire loop embodiment of the heart valve prosthesis partially ejected, and partially disposed within, a delivery catheter and having an annulus support loop and an upper and lower tension arm formed as a unitary or integral part. FIG. 17 shows how a valve can be partially delivered for positioning in the annulus. The lower tension arm 144 can be used to navigate through the tricupid leaflets and chordae tendinae while the valve body, the tubular frame, 102 is still within the steerable IVC delivery catheter 118.

Figure 18:
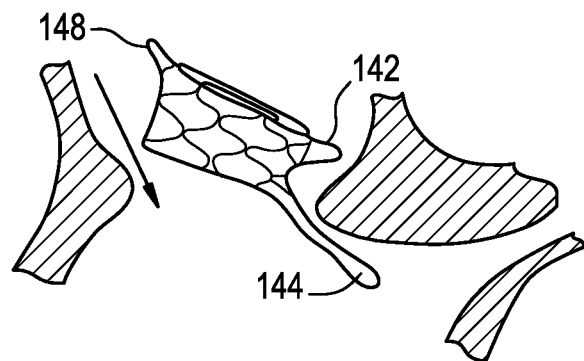
FIG. 18 is an illustration of a plan view of a heart valve prosthesis partially mounted within the valve annulus.

FIG. 18 is an illustration of a plan view of a heart valve prosthesis partially mounted within the valve annulus. By using the side-loaded valve of the present invention, the distal side of the prosthesis 142, 144 can be mounted against the anterior aspect of the native annulus, and valve function can be assessed. By allowing two pathways for blood flow, the first through the native valve near the posterior leaflet, and the second through the central aperture of the prosthetic valve, a practitioner can determine if the heart is decompensating or if valve function is less than optimal.

Figure 19:
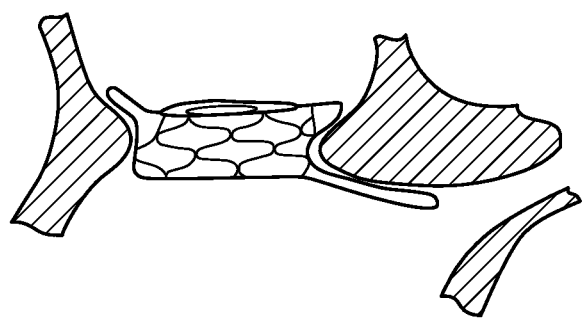
FIG. 19 is an illustration of a plan view of a heart valve prosthesis completely seated within the valve annulus.

FIG. 19 is an illustration of a plan view of a heart valve prosthesis completely seated within the valve annulus. FIG. 19 shows that the valve can be secured in place once the valve function assessment shows that the deployment is successful. Importantly, since the valve is a low-profile valve, and fits easily within a standard, e.g. 8-12 mm, delivery catheter without requiring the forceful loading of typical transcatheter valves, the side-loading valve can be easily retrieved using the same delivery catheter that is used to deploy the valve.

Figure 20:
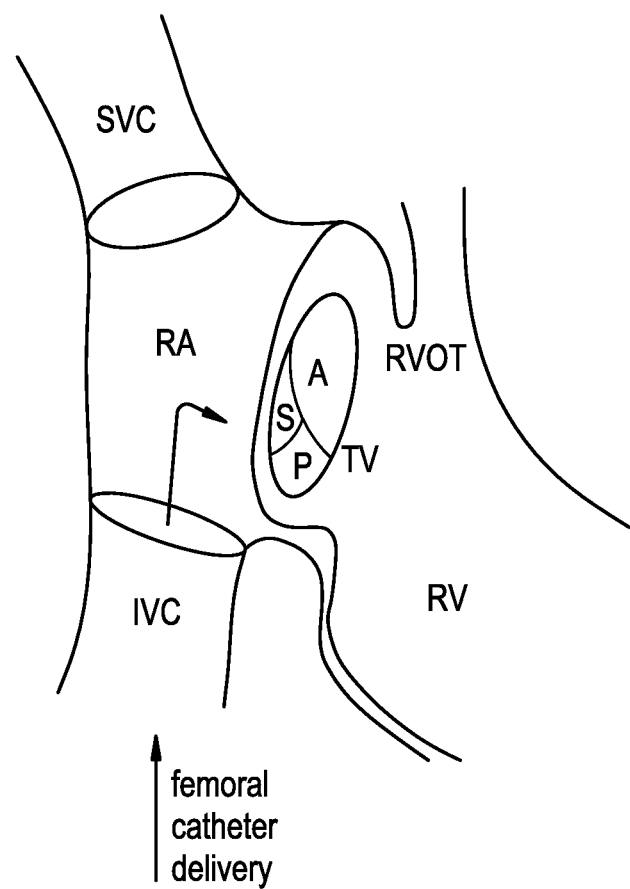
FIG. 20 is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet(S), the right ventricle (RV), and the right ventricular outflow tract (RVOT).

FIG. 20 is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet (S), the right ventricle (RV), and the right ventricular outflow tract (RVOT).

Figure 21:
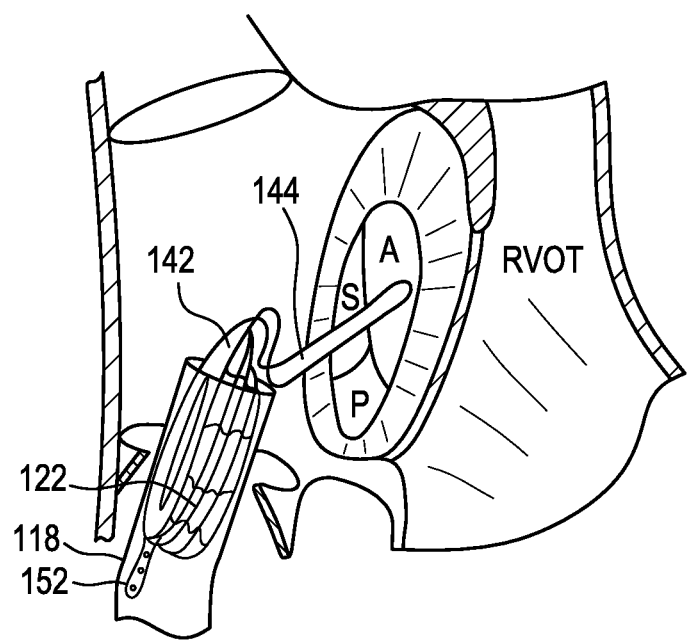
FIG. 21 is an illustration of a heart valve prosthesis having a wire-frame according to the present invention being delivered to tricuspid valve annulus.

FIG. 21 is an illustration of a heart valve prosthesis according to the present invention being delivered to tricuspid valve annulus. FIG. 21 shows wire-frame lower tension arm 144 ejected from the delivery catheter 118 and being directed through the annulus and towards the right ventricular outflow tract. FIG. 21 shows an embodiment of an accordion-compressed low-profile valve 122 and shows the lower tension arm directed towards the anterior leaflet for placement into the RVOT.

Figure 22:
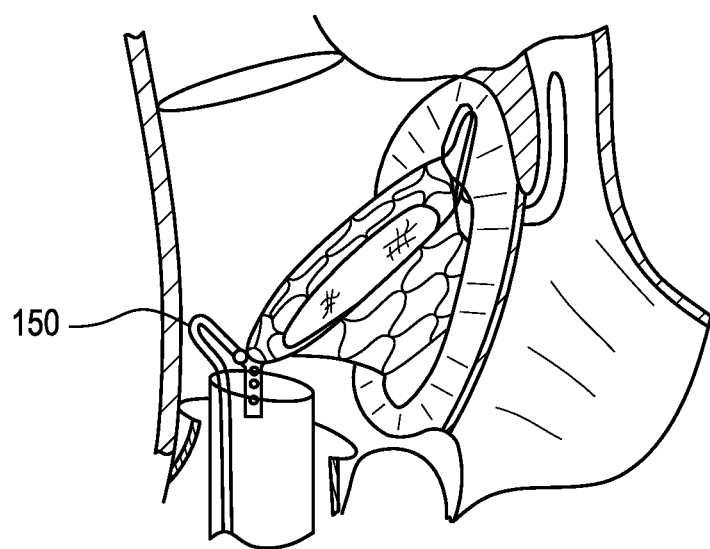
FIG. 22 is an illustration of a heart valve prosthesis having a wire-frame according to the present invention being delivered to tricuspid valve annulus.

FIG. 22 is an illustration of a heart valve prosthesis according to the present invention being delivered to tricuspid valve annulus. FIG. 22 shows wire-frame lower tension arm 144 and upper tension arm 142 ejected from the delivery catheter 118, the lower tension arm directed through the annulus and into the right ventricular outflow tract, and the upper tension arm staying in a supra-annular position, and causing a passive, structural anchoring of the distal side of the valve about the annulus. FIG. 22 also shows steerable anchoring catheter 150 attached to a proximal anchoring tab 152. While the valve is held in a pre-seating position, the valve can be assessed, and once valve function and patient conditions are correct, the steerable anchoring catheter can push the proximal side of the valve from its oblique angle, down into the annulus. The steerable anchoring catheter can then install one or more anchoring elements 152.

Figure 23:
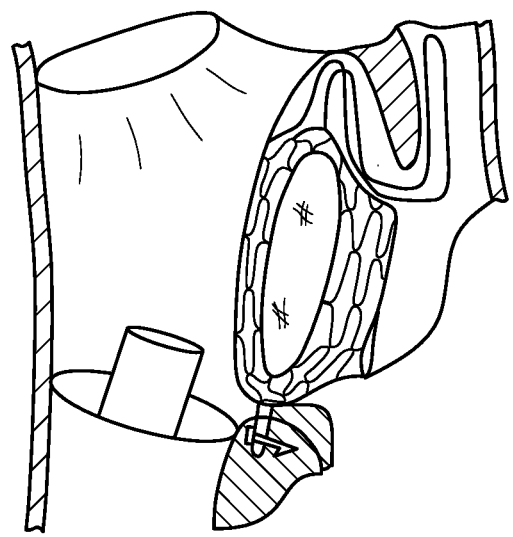
FIG. 23 is an illustration of a heart valve prosthesis having a wire-frame according to the present invention that has been delivered to tricuspid valve annulus.

FIG. 23 is an illustration of a heart valve prosthesis according to the present invention being delivered to tricuspid valve annulus. FIG. 23 shows the entire valve ejected from the delivery catheter, the wire-frame lower tension arm directed through the annulus and into the right ventricular outflow tract, and the upper wire-frame tension arm staying in a supra-annular position, and causing a passive, structural anchoring of the distal side of the valve about the annulus, and at least one tissue anchor anchoring the proximal side of the prosthesis into the annulus tissue.

Figure 24:
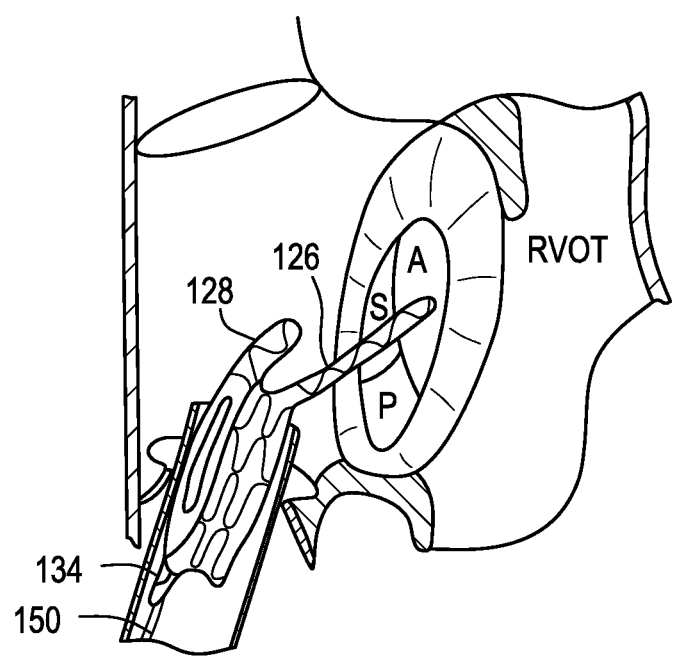
FIG. 24 is an illustration of a heart valve prosthesis having a braided/laser cut-frame according to the present invention being delivered to tricuspid valve annulus.

FIG. 24 is an illustration of a heart valve prosthesis according to the present invention being delivered to tricuspid valve annulus. FIG. 24 shows braided/laser cut-frame lower tension arm 126 ejected from the delivery catheter 118 and being directed through the annulus and towards the right ventricular outflow tract.

Figure 25:
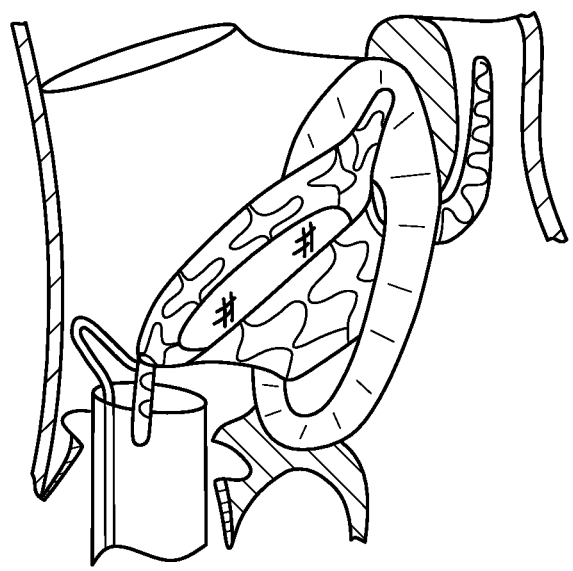
FIG. 25 is an illustration of a heart valve prosthesis having a braided/laser cut-frame according to the present invention being delivered to tricuspid valve annulus.

FIG. 25 is an illustration of a heart valve prosthesis according to the present invention being delivered to tricuspid valve annulus. FIG. 25 shows braided/laser cut-frame lower tension arm 126 and upper tension arm 128 ejected from the delivery catheter 118, the lower tension arm directed through the annulus and into the right ventricular outflow tract, and the upper tension arm staying in a supra-annular position, and causing a passive, structural anchoring of the distal side of the valve about the annulus.

Figure 26:
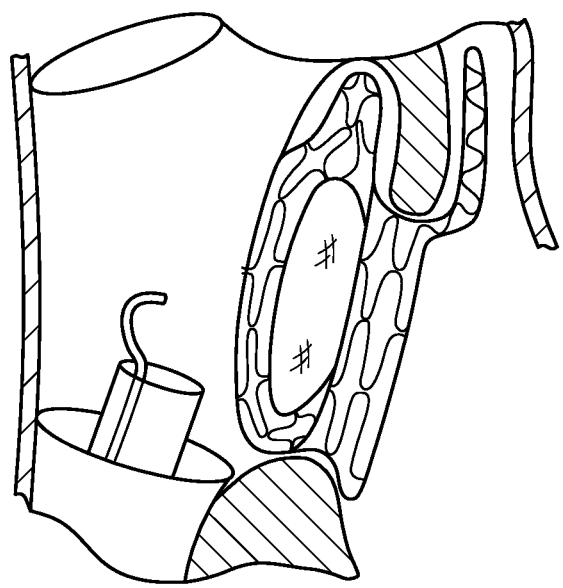
FIG. 26 is an illustration of a heart valve prosthesis having a braided/laser cut-frame according to the present invention that has been delivered to tricuspid valve annulus.

FIG. 26 is an illustration of a heart valve prosthesis according to the present invention being delivered to tricuspid valve annulus. FIG. 26 shows the entire braided/laser cut-frame valve 102 ejected from the delivery catheter 118, the lower tension arm directed through the annulus and into the right ventricular outflow tract, and the upper tension arm staying in a supra-annular position, and causing a passive, structural anchoring of the distal side of the valve about the annulus, and at least one tissue anchor anchoring the proximal side of the prosthesis into the annulus tissue.

Figure 27:
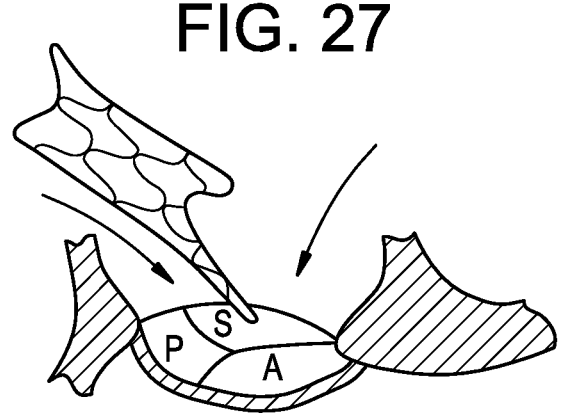
FIG. 27 is an illustration of a heart valve prosthesis according to the present invention being delivered to tricuspid valve annulus and shows step 1 in a valve assessment process.

FIG. 27 is an illustration of a heart valve prosthesis according to the present invention being delivered to tricuspid valve annulus and shows step 1 in a valve assessment process. FIG. 27 shows braided/laser cut-frame lower tension arm ejected from the delivery catheter and being directed through the annulus and towards the right ventricular outflow tract.

Figure 28:
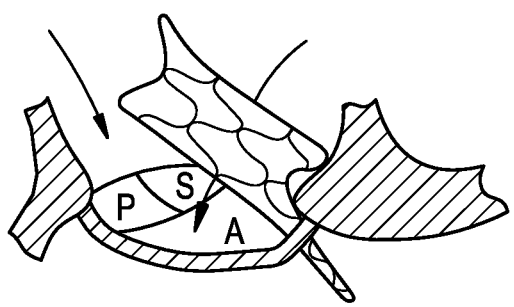
FIG. 28 is an illustration of a heart valve prosthesis according to the present invention being delivered to tricuspid valve annulus, and shows Step 2 in a valve assessment process.

FIG. 28 is an illustration of a heart valve prosthesis according to the present invention being delivered to tricuspid valve annulus, and shows Step 2 in a valve assessment process. FIG. 28 shows braided/laser cut-frame lower tension arm and upper tension arm ejected from the delivery catheter, the lower tension arm directed through the annulus and into the right ventricular outflow tract, and the upper tension arm staying in a supra-annular position, and causing a passive, structural anchoring of the distal side of the valve about the annulus. FIG. 28 shows that a steerable anchoring catheter can hold the valve at an oblique angle in a pre-attachment position, so that the valve can be assessed, and once valve function and patient conditions are correct, the steerable anchoring catheter can push the proximal side of the valve from its oblique angle, down into the annulus. The steerable anchoring catheter can then install one or more anchoring elements.

Figure 29:
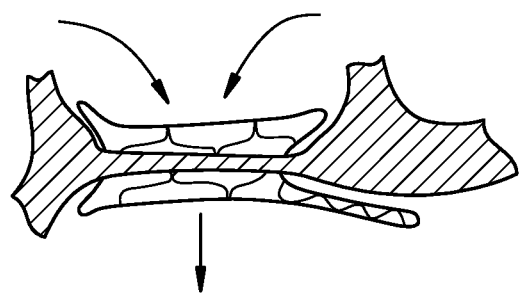
FIG. 29 is an illustration of a heart valve prosthesis according to the present invention that has been delivered to tricuspid valve annulus, and shows Step 3 in a valve assessment process.

FIG. 29 is an illustration of a heart valve prosthesis according to the present invention that has been delivered to tricuspid valve annulus, and shows Step 3 in a valve assessment process. FIG. 29 shows the entire braided/laser cut-frame valve ejected from the delivery catheter, the lower tension arm directed through the annulus and into the right ventricular outflow tract, and the upper tension arm staying in a supra-annular position, and causing a passive, structural anchoring of the distal side of the valve about the annulus, and at least one tissue anchor anchoring the proximal side of the prosthesis into the annulus tissue.

Figure 30:
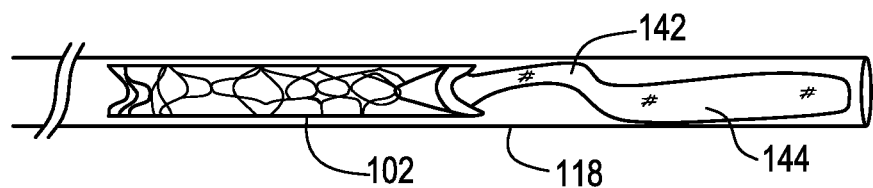
FIG. 30 is an illustration of a wire-frame embodiment of a heart valve prosthesis according to the present invention in a compressed, intra-catheter phase.

FIG. 30 is an illustration of a heart valve prosthesis according to the present invention in a compressed, intra-catheter phase. The lower and upper tension arms 144, 142 are elongated to the right, and the prosthetic valve 102 is shown laterally compressed in the delivery catheter 118. The lateral compression is a function of the use of minimal structural materials, e.g. a minimal inner valve sleeve 110, and the relatively short height of the outer cylindrical frame 102. This lateral delivery provides for very large, e.g. up to 80 mm or more, valve prosthesis' to be delivered. The lateral delivery also avoids the need to perform a 90 degree right turn when delivering a valve using the IVC femoral route. This sharp delivery angle has also limited the size and make up of prior valve prosthesis', but is not a problem for the inventive valve herein.

Figure 31:
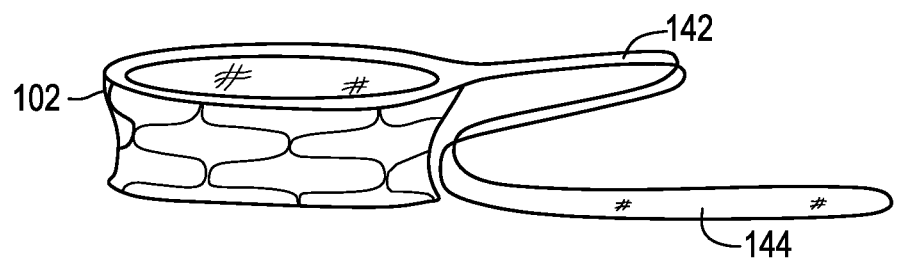
FIG. 31 is an illustration of a profile, or plan, view of a wire-frame embodiment of the heart valve prosthesis according to the present invention in a un-compressed, postcatheter-ejection phase.

FIG. 31 is an illustration of a profile, or plan, view of a wire-frame embodiment of the heart valve prosthesis according to the present invention in a un-compressed, postcatheter-ejection phase. FIG. 31 shows an embodiment where the upper wire-frame tension arm 142 is attached to the tubular frame 102, but the lower tension arm 144 is shaped in an S-shape and connects only to the upper tension arm 142.

Figure 32:
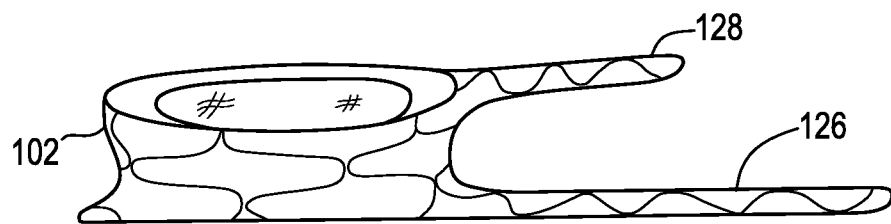
FIG. 32 is an illustration of a profile, or plan, view of a braided or laser-cut frame embodiment of the heart valve prosthesis according to the present invention in a un-compressed, post-catheter-ejection phase.

FIG. 32 is an illustration of a profile, or plan, view of a braid or laser-cut frame embodiment of the heart valve prosthesis according to the present invention in a un-compressed, post-catheter-ejection phase. FIG. 32 shows an embodiment where the upper braid or laser-cut tension arm 128 is attached to the upper edge of the tubular frame 102, and the lower tension arm 126 is attached to the lower edge of the tubular frame 102.

FIG. 33 is an illustration of a TOP view of a heart valve prosthesis according to the present invention having covered wire loop for the upper tension arm(s). FIG. 24 shows the tubular frame 102 having an inner sleeve 110 sewn into the central aperture 106, with the two (2) panels extending downward (into the page) in a ventricular direction. FIG. 33 shows the upper tension arms 142 oriented towards the anterior leaflet side of the atrial floor, shown in dashed outline.

FIG. 34 is an illustration of a PLAN view of a heart valve prosthesis according to the present invention having a wire loop construction for the upper 142 and lower 144 tension arms.

FIG. 35 is an illustration of a CUT-AWAY PLAN view of a heart valve prosthesis according to the present invention, and shows the inner panel valve sleeve 110 mounted within the inner space defined by the tubular frame.

FIG. 36 is an illustration of a BOTTOM view of a heart valve prosthesis according to the present invention having a covered wire loop for the lower tension arm 144. FIG. 36 shows the tubular frame 102 having an inner sleeve 110 sewn into the central aperture, with the two (2) panels extending upward (out of the page) in a ventricular direction. FIG. 36 shows the lower tension arm 144 oriented towards the anterior leaflet side of the ventricular ceiling, shown in dashed outline.

FIG. 37 is an illustration of a TOP view of a heart valve prosthesis according to the present invention having covered braid or laser-cut frame 102 for the upper tension arm 128. FIG. 37 shows the tubular frame 102 having an inner sleeve 110 sewn into the central aperture, with the two (2) panels extending downward (into the page) in a ventricular direction. FIG. 37 shows the upper tension arm 128 oriented towards the anterior leaflet side of the atrial floor, shown in dashed outline.

FIG. 38 is an illustration of a PLAN view of a heart valve prosthesis according to the present invention having a braid or laser-cut frame construction 102 for the upper and lower tension arms 128, 126.

FIG. 39 is an illustration of a CUT-AWAY PLAN view of a heart valve prosthesis according to the present invention, and shows the inner panel valve sleeve 110 mounted within the inner space defined by the tubular frame 102.

FIG. 40 is an illustration of a BOTTOM view of a heart valve prosthesis according to the present invention having a covered braid or laser-cut frame for the lower tension arm. FIG. 40 shows the tubular frame 102 having an inner sleeve 110 sewn into the central aperture, with the two (2) panels extending upward (out of the page) in a ventricular direction. FIG. 40 shows the lower tension arm 126 oriented towards the anterior leaflet side of the ventricular ceiling, shown in dashed outline.

FIG. 41 is an illustration of a heart valve prosthesis according to the present invention having a wire loop construction for the tubular frame 102, with two vertical support posts 154 extending down the edge on opposing sides of the sleeve 110. During compression into the delivery catheter 118 (not shown), the posts 154 are engineered to fold horizontally during compression, and to elastically unfold during ejection to deploy the valve sleeve 110.

FIG. 42 is an illustration of a CUT-AWAY PLAN view of a heart valve prosthesis according to the present invention, and shows a two-post embodiment 154 of the inner panel valve sleeve 110 mounted within the inner space defined by the tubular frame 102.

FIG. 43 is an illustration of a CUT-AWAY PLAN view of a heart valve prosthesis according to the present invention, and shows a three-panel, three-post embodiment of the inner panel valve sleeve mounted within the inner space defined by the tubular frame.

FIG. 44 is an illustration of a TOP view of a heart valve prosthesis according to the present invention having braid or laser-cut wire frame 102 and shown mounted within a cross-sectional view of the atrial floor at the annulus.

FIG. 45 is an illustration of a BOTTOM view of a heart valve prosthesis according to the present invention having braid or laser-cut wire frame 102 for a lower tension arm and shown mounted within a cross-sectional view of the ventricular ceiling at the annulus. FIG. 45 shows the two panel valve sleeve 110 in an open position 106, e.g. atrial systole and ventricular diastole. FIG. 41 shows RVOT as a darkened circle.

FIG. 46 is an illustration of a PLAN view of an embodiment of the prosthetic valve shown in a compressed configuration within a delivery catheter. FIG. 46 shows the tubular frame wall rolled-over, outwardly, resulting in a 50% reduction in height of the catheter-housed valve. The low profile, side-loaded valves of the present invention do not require the aggressive, strut-breaking, tissue-tearing, stitch-pulling forces that traditional transcatheter valves are engineered to mitigate.

FIG. 47 is an illustration of a cross-sectional view of one embodiment of a compressed valve within a delivery catheter 118. This cross-sectional end view shows one embodiment of a single-fold compression configuration where the tubular frame wall 102 and attached two-panel sleeve 110 are rolled-over, outwardly, resulting in a 50% reduction in height, and providing the ability to fit within the inner diameter of a 1 cm (10 mm) delivery catheter.

FIG. 48 is an illustration of a cross-sectional view of another embodiment of a compressed valve within a delivery catheter. This cross-sectional end view shows another embodiment of a single-fold compression configuration where the tubular frame wall and attached two-panel sleeve are folded-over, outwardly, resulting in a 50% reduction in height, and providing the ability to fit within the inner diameter of a 1 cm (10 mm) delivery catheter.

FIG. 49 is an illustration of a cross-sectional view of an embodiment of the prosthetic valve to further illustrate how the folding and rolling configurations can be effectuated due to the minimal material requirement of the low-profile, side-loaded valve 102, 110.

FIG. 50 (a)-(b)-(c) is an illustration of a sequence of a low-profile valve being rolled into a configuration for placement within a delivery catheter. Tubular frame 102 having aperture 106 supports sleeve 110.

FIG. 51 is an illustration of an END-VIEW of a low-profile valve that has been longitudinally rolled and loaded within a delivery catheter 118, and show frame 102 and sleeve 110.

FIG. 52 is an illustration of a rotational lock embodiment of the present invention where the prosthetic valve is delivered to the native annulus with an off-set sub-annular tension arm/tab 126 positioned below the native annulus, and an off-set supra-annular tension arm/tab 128 positioned above the native annulus, while the tubular frame 102 is partially rolled off-set from the annular plane along a longitudinal axis.

FIG. 53 is an illustration of a rotational lock embodiment of the present invention where the prosthetic valve is delivered to the native annulus with an off-set sub-annular tension arm/tab 126 positioned below the native annulus, and an off-set supra-annular tension arm/tab 128 positioned above the native annulus, while the tubular frame 102 is rolled into functional position parallel to the annular plane. Once the valve is rolled into position, and the tension arms are locked against the sub-annular and supra-annular tissues, the valve can also be further anchored using traditional anchoring elements as disclosed herein.

FIG. 54 is an illustration of a two-panel embodiment of an inner valve sleeve 110.

FIG. 55 is an illustration of one embodiment of an inner valve sleeve 110 having two rigid support posts 154.

FIG. 56 is an illustration of a three-panel embodiment of an inner valve sleeve 110.

FIG. 57 is an illustration of a three-panel embodiment of an inner valve sleeve 110 having three rigid support posts 154.

FIG. 58 is a flowchart describing one set of method steps for delivery of a low-profile, side-loaded prosthetic valve.

FIG. 59(a)-(c) is an illustration of a plan view of a tissue anchor having a floating radio-opaque marker. This figure shows the tissue anchor accessing the annular tissue withe the radio-opaque marker at the distal end of the anchor and in contact with the atrial surface of the annular tissue. This figure shows the tissue anchor advancing into the annular tissue with the radio-opaque marker threaded onto the tissue anchor and maintaining position on the atrial surface of the annular tissue. This figure shows the tissue anchor completely advanced into the annular tissue such that the tissue anchor and the threaded floating marker are now adjacent, indicating the desired depth, tension, and/or plication of the tissue anchor with respect to the annular tissue.

FIG. 60 is an illustration of a plan view of a tissue anchor having a straight thread and a constant pitch.

FIG. 61 is an illustration of a plan view of a tissue anchor having a straight thread and a variable pitch.

FIG. 62 is an illustration of a plan view of a tissue anchor having a tapered thread and a constant pitch.

FIG. 63 is an illustration of a plan view of a tissue anchor having a sunken taper thread and a variable pitch.

FIG. 64 is an illustration of Step 1 of a 4 step process for clipping a low profile valve to annular tissue, as shown here in a non-limiting example of clipping to a proximal or anterior side of the native annulus. FIG. 64 shows a low profile valve being inserted into the valve annulus and low profile valve having an integral anchor delivery conduit or channel with an anchor disposed in the lumen of the channel and an anchor delivery catheter attached to the anchor.

FIG. 65 is an illustration of Step 2 of a 4 step process for clipping a low profile valve to annular tissue, as shown here in a non-limiting example of clipping to a proximal or anterior side of the native annulus. FIG. 65 shows a low profile valve completely deployed within the valve annulus and an integral anchor delivery conduit or channel with an anchor disposed in the lumen of the channel and an anchor delivery catheter attached to the anchor.

FIG. 66 is an illustration of Step 3 of a 4 step process for clipping a low profile valve to annular tissue, as shown here in a non-limiting example of clipping to a proximal or anterior side of the native annulus. FIG. 66 shows the anchor being pushed out of the lumen of the delivery conduit or channel and into the annular tissue.

FIG. 67 is an illustration of Step 4 of a 4 step process for clipping a low profile valve to annular tissue, as shown here in a non-limiting example of clipping to a proximal or anterior side of the native annulus. FIG. 67 shows the anchor in a locked position after being pushed out of the lumen of the delivery conduit or channel and into the annular tissue, thus anchoring the proximal side of the low profile valve.

FIG. 68 is an illustration of Step 1 of a 5 step process for clipping a low profile valve to annular tissue, as shown here in a non-limiting example of clipping to a proximal or anterior side of the native annulus. FIG. 68 shows catheter delivery of an attachment wire with the clip housed within the lumen of the clip delivery catheter.

FIG. 69 is an illustration of Step 2 of a 5 step process for clipping a low profile valve to annular tissue, as shown here in a non-limiting example of clipping to a proximal or anterior side of the native annulus. FIG. 69 shows the clip delivery catheter inserted into an intra-annular space and shows an attachment wire and shows the clip housed within the lumen of the clip delivery catheter.

FIG. 70 is an illustration of Step 3 of a 5 step process for clipping a low profile valve to annular tissue, as shown here in a non-limiting example of clipping to a proximal or anterior side of the native annulus. FIG. 70 shows a receiver element ejected from the delivery catheter and positioned behind tissue to be captured.

FIG. 71 is an illustration of Step 4 of a 5 step process for clipping a low profile valve to annular tissue, as shown here in a non-limiting example of clipping to a proximal or anterior side of the native annulus. FIG. 71 shows an anchor element piercing the annular tissue and inserting into a receiver element.

FIG. 72 is an illustration of Step 5 of a 5 step process for clipping a low profile valve to annular tissue, as shown here in a non-limiting example of clipping to a proximal or anterior side of the native annulus. FIG. 72 shows that the clip delivery catheter is withdrawn and the anchor element and receiver element are connected to the annular tissue and a also connected by connector wire to the low profile valve.

FIG. 73 is an illustration of one embodiment of a partial cut-away interior view of a tri-leaflet embodiment of a low-profile, e.g. 8-20 mm, side-loaded prosthetic valve.

FIG. 74 is an illustration of another embodiment of a partial cut-away interior view of a tri-leaflet embodiment of a low-profile, e.g. 8-20 mm, side-loaded prosthetic valve.

FIG. 75 is an illustration of a top view of a tri-leaflet embodiment of a low-profile, e.g. 8-20 mm, side-loaded prosthetic valve.

FIG. 76 is an illustration of the trans-septal (femoral-IVC) delivery of a low-profile, e.g. 8-20 mm, side-loaded prosthetic MITRAL valve shown partially housed within the delivery catheter, and partially ejected for deployment into the native mitral annulus.

FIG. 77 is an illustration of a low-profile, e.g. 8-20 mm, side-loaded prosthetic MITRAL valve shown housed within the delivery catheter.

FIG. 78 is an illustration of a low-profile, e.g. 8-20 mm, side-loaded prosthetic MITRAL valve shown partially housed within a delivery catheter and partially latterally ejected from the delivery catheter and positioned for deployment against the anterior side of the native mitral annulus.

FIG. 79 is an illustration of a low-profile, e.g. 8-20 mm, side-loaded prosthetic MITRAL valve shown ejected from the delivery catheter and positioned against the anterior side of the native mitral annulus.

FIG. 80 is an illustration of a side or plan view of a low-profile, e.g. 8-20 mm, side-loaded prosthetic valve shown deployed into the native MITRAL annulus.

FIG. 81 is a flowchart showing a preferred embodiment of a method for side delivery of implantable prosthetic valve to a desired location in the body, the method comprising the steps:

advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

FIG. 82 is a flowchart showing a preferred embodiment of a method for side or orthogonal loading an implantable prosthetic valve into a delivery catheter, the method comprising the steps:

loading an implantable prosthetic valve into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

Figure 83A:
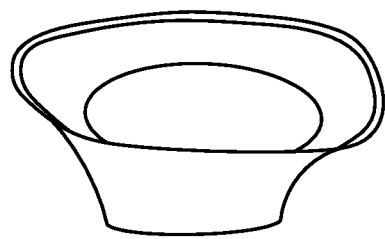
Figure 83B:
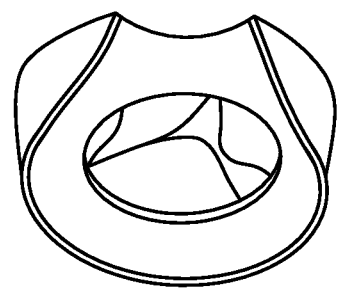
Figure 83C:
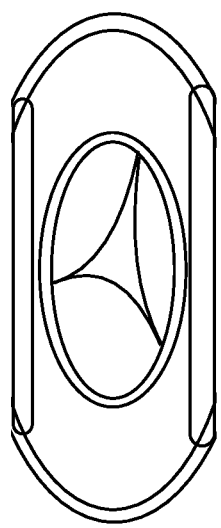
Figure 83D:

FIG. 83(a)-(d) is an illustration of one embodiment of the invention showing a four step (a)-(d) process for compressing a prosthetic valve to provide a long-axis that is coplanar or parallel with the length-wise axis of a delivery catheter. FIG. 83 shows that a prosthetic valve having a tubular frame made of a cuff and a trans-annular tubular section, having a flow control component mounted within the tubular frame and configured to permit blood flow in a first direction through an inflow end of the valve and block blood flow in a second direction, opposite the first direction, through an outflow end of the valve, is compressible along a long-axis that is parallel to a length-wise axis of a delivery catheter. FIG. 83 shows that the valve is compressible to a compressed configuration for introduction into the body using a delivery catheter where said compressed configuration has a long-axis that is perpendicular to the blood flow direction axis, i.e. oriented at an intersecting (orthogonal) angle of between 45-135 degrees, e.g. 90 degrees, to the first (blood flow) direction, and where the long-axis of the compressed configuration of the valve is substantially parallel to a length-wise cylindrical axis of the delivery catheter, wherein the valve has a height of about 5-60 mm and a diameter of about 25-80 mm. FIG. 83 (a) shows an illustration of an uncompressed valve. FIG. 83(b) shows an illustration of an initial rolling or folding of the cuff. The folding or rolling can be inwards as shown here, or may be outwardly rolled, or may also be flattened together for rolling the the entire valve rolled up from bottom to top. FIG. 83(c) shows an illustration of a valve that has been rolled or folded, using multiple folds or rolls, along a long-axis into a tube-shape. FIG. 83(d) shows an illustration of a completely compressed valve, that has been folded or rolled, using a compression accessory, and which is then loaded into the delivery catheter. Such a compressed valve may be self-expanding when released from the delivery catheter using shape-memory alloys, or the valve may be balloon expanded in a secondary process once the valve is released from the delivery catheter.

PARTS LIST 100 side-loading transcatheter heart valve replacement
102 a ring-shaped tubular frame
104 a braid, wire, or laser-cut wire frame
106 substantially circular central aperture,
108 biocompatible material cover for frame;
110 valve sleeve, aka a collapsible flow control sleeve
112,114 valve sleeve panels
116 a reciprocating closable channel from a heart atrium to a heart ventricle;
118 a transcatheter implantation (delivery) catheter
120 an internal diameter from 22 Fr (7.33 mm) to 34 Fr (11.33 mm),
122 compressed tubular frame oriented parallel to length-wise axis delivery catheter
124 length-wise axis of a delivery catheter.
126 lower tension arm/tab, braid/laser
128 upper tension arm/tab, braid/laser
130 proximal sealing cuff
132 hourglass annular seal
134 upper proximal tab
136 lower proximal tab
138 screw anchor
140 wire tubular frame
142 upper tension arm/tab, wire
144 lower tension arm/tab, wire 146 substantially circular central aperture
148 upper proximal tab, wire
150 steerable anchoring/deployment catheter
152 screw/anchor tab
154 valve sleeve support posts
156 sleeve terminus aperture Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A device, comprising:
   a side-delivered transcatheter prosthetic heart valve having a height of 8-20 millimeters (mm) and a diameter of 40-80 mm,
   wherein the valve is compressible to a compressed configuration for side-delivery into a tricuspid or mitral annulus of a heart using a delivery catheter,
   the compressed configuration having a long-axis substantially parallel to a length-wise cylindrical axis of the delivery catheter, the long-axis substantially perpendicular to blood flow through the valve,
   the valve having an outer frame comprising an upper collar attached around a top edge of a trans-annular tubular section, and a lower collar attached around at least a lower portion of the trans-annular tubular section, the upper collar and the lower collar combining to sandwich or compress the tricuspid or mitral annulus to seal the annulus from perivalvular leaks, and
   a flow control component mounted within a lumen of the outer frame, the flow control component having three leaflets joined to a plurality of rigid support posts, the flow control component configured to permit blood flow in a first direction through an inflow end of the valve and block blood flow in a second direction, opposite the first direction, through an outflow end of the valve.

2. The device of claim 1, wherein the outer frame is configured with a roughly tubular configuration being centric or radially symmetrical.

3. The device of claim 1, wherein the outer frame is configured to provide an upper atrial cuff or flange for atrial sealing and a lower trans-annular tubular section that conforms to the native annulus, the outer frame being eccentric or radially asymmetrical.

4. The device of claim 1, wherein the flow control component has a height of 10-20 mm and a diameter of about 25 mm.

5. The device of claim 1, wherein the valve has a compressed height of 5-12 mm and an expanded height of 8-20 mm, a compressed width of 8-12 mm and an expanded width of 40-80 mm, and a length of 40-80 mm.

6. The device of claim 1, wherein the delivery catheter is 8-12 mm in diameter or 24-36 French (Fr).

7. The device of claim 1, wherein the outer frame has a biocompatible covering.

8. The device of claim 1, wherein the valve includes an anchor selected from the group consisting of: a 10-40 mm distal subannular anchoring tension arm attached to the outer frame, a 10-30 mm distal supra-annular anchoring tension arm attached to the outer frame, a proximal tissue anchor attached to the outer frame, a proximal supra-annular anchoring tension arm, and an anchor integrated within the outer frame structure.

9. The device of claim 8, wherein the anchor has a biocompatible covering.

10. The device of claim 1, wherein the valve in the compressed configuration has a long-axis oriented at an intersecting angle of between 45-135 degrees to the first direction, and is expandable to an expanded configuration having a long-axis oriented at an intersecting angle of between 45-135 degrees to the first direction.

11. The device of claim 1, wherein the valve in the compressed configuration is selected from an accordion-folded compressed configuration, a rolled compressed configuration, a folded compressed configuration, and a lateral compressed configuration.

12. The device of claim 1, wherein the valve height is 10 mm.

13. The device of claim 1, wherein the outer frame forms a two part framework, a first part comprises a flared atrial cuff joined to a second part that comprises a trans-annular tubular segment, wherein the cuff is joined to the trans-annular tubular segment around a circumference of a top edge of the trans-annular tubular segment.

14. The device of claim 1, wherein the outer frame is comprised of a braided, wire, or laser-cut wire frame, and
   wherein the outer frame has an inner surface and an outer surface, the inner surface and the outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

15. The device of claim 1, wherein the outer frame has a side profile of a flat cone shape or an hourglass shape.

16. The device of claim 1, wherein the flow control component has an internal diameter of 20-60 mm and a height of 8-20 mm, and the leaflets are made from pericardial material joined to form a rounded cylinder at an inflow end and having a closable aperture at an outflow end.

17. The device of claim 1, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

18. The device of claim 1, wherein the valve has a distal subannular anchoring tension arm comprised of a wire loop or wire frame, an integrated frame section, or a stent.

19. The device of claim 1, wherein the valve has a distal supra-annular anchoring tension arm attached to a distal upper edge of the outer frame, the distal supra-annular anchoring tension arm comprised of a wire loop or wire frame extending about 2-20 mm away from the outer frame.

20. The device of claim 1, wherein the valve has a proximal subannular anchoring tension arm attached to a lower proximal side wall of the outer frame and at least one tissue anchor connected to the outer frame for engaging native tissue.

21. The device of claim 1, wherein the trans-annular tubular section has a shape selected from the group consisting of: a ring shape, a cylinder shape, a conical tube shape, a flat cone shape, an inverted flat cone shape, a concave cylinder, a convex cylinder, an angular hourglass shape, a curved hourglass shape, a ring or cylinder having a flared top or bottom portion, a complex shape to fit an anatomical structure of a tricuspid annulus with a rounded ellipse circumference and having a vertical septal wall portion with concave posterior and anterior wall portions, and a complex shape to fit an anatomical structure of a mitral annulus with a hyperbolic paraboloid circumference and having a vertical septal wall portion with concave posterior and anterior wall portions.

22. A method for orthogonal delivery of an implantable prosthetic valve between a ventricle and an atrium of a heart, the method comprising:
    advancing a delivery catheter containing the prosthetic valve of claim 1 in the compressed configuration to the atrium of the heart;
    releasing a distal portion of the prosthetic valve from a lumen of the delivery catheter and delivering the distal portion of the trans-annular tubular section to the distal side of the annulus of the native valve; and
    releasing the remainder of the prosthetic valve from the lumen of the delivery catheter to allow the prosthetic valve to expand to the expanded configuration such that the trans-annular tubular section is disposed within the annulus of the native valve, and
    wherein releasing the distal portion of the prosthetic valve from the lumen of the delivery catheter comprises pulling the distal portion out of the delivery catheter using a rigid elongated pushing rod that is releasably connected to the distal portion, wherein advancing the pushing rod away from the delivery catheter pulls the prosthetic valve out of the delivery catheter.

23. The method of claim 22, further comprising:
    anchoring one or more anchors attached to the prosthetic valve to native tissue.

24. The method of claim 22, wherein the distal portion of the prosthetic valve includes a distal subannular anchoring tension arm, the method further comprising:
    positioning the distal subannular anchoring tension arm of the prosthetic valve into a subannular position, and the upper collar providing a supra-annular downward force in the direction of the ventricle and the distal subannular anchoring tension arm providing a subannular upward force in the direction of the atrium.

25. The method of claim 24, further comprising:
    anchoring a portion of the prosthetic valve opposite to the distal subannular anchoring tension arm to the annulus of the native valve.

26. The method of claim 22, further comprising, between the releasing the distal portion of the prosthetic valve and the releasing the remainder of the prosthetic valve from the lumen of the delivery catheter, allowing blood to flow from the atrium to the ventricle both through the native valve and through the prosthetic valve.

27. The method of claim 22, wherein the distal portion of the prosthetic valve includes a distal subannular anchoring tension arm, the delivery catheter includes the elongated pushing rod disposed in the lumen of the delivery catheter and having a distal end engaged with the distal subannular anchoring tension arm of the prosthetic valve, and
    wherein the releasing the distal portion of the prosthetic valve from the lumen of the delivery catheter includes advancing the pushing rod distally through the lumen to pull the distal subannular anchoring tension arm out of the lumen of the delivery catheter.

28. The method of claim 22, wherein the native valve is a tricuspid valve, the atrium is the right atrium, and the ventricle is the right ventricle, the distal portion of the prosthetic valve includes a distal subannular anchoring tension arm, and
    wherein the releasing the distal portion of the prosthetic valve includes disposing at least a distal portion of the distal subannular anchoring tension arm into a right ventricular outflow tract of the right ventricle.

29. The method of claim 22, wherein the native valve is a tricuspid valve, the atrium is the right atrium, and the ventricle is the right ventricle, the distal portion of the prosthetic valve includes a distal subannular anchoring tension arm, the prosthetic valve further includes a distal supra-annular anchoring tension arm coupled to and extending laterally from the outer frame, the method further comprising:
    disposing at least a distal portion of the distal supra-annular anchoring tension arm on the right atrium side of the annulus of the tricuspid valve, the distal supra-annular anchoring tension arm providing a supra-annular downward force in a direction of the right ventricle and the distal subannular anchoring tension arm providing a subannular upward force in a direction of the right atrium.

30. The method of claim 22, wherein the native valve is a mitral valve, the atrium is the left atrium, and the ventricle is the left ventricle, the distal portion of the prosthetic valve includes a distal subannular anchoring tension arm, and
    wherein the releasing the distal portion of the prosthetic valve includes disposing at least a distal portion of the distal subannular anchoring tension arm under an anterior portion of the annulus of the mitral valve.

* * * * *